United States Patent [19]
Adam et al.

[11] Patent Number: 6,043,366
[45] Date of Patent: Mar. 28, 2000

[54] 1,3,8,-TRIAZA SPIRO (4,5)DECAN-4-ON DERIVATIVES

[75] Inventors: Geo Adam, Schopfheim, Germany; Andrea Cesura, Basel, Switzerland; Caido Galley, Rheinfelden, Germany; François Jenck, Riedisheim, France; Stephan Röver, Inzlingen; Jürgen Wichmann, Steinen, both of Germany

[73] Assignee: Hoffman-La Roche Inc., Nutley, N.J.

[21] Appl. No.: 09/204,184

[22] Filed: Dec. 3, 1998

[30] Foreign Application Priority Data

Dec. 5, 1997 [EP] European Pat. Off. ............. 97121427

[51] Int. Cl.⁷ ...................... C07D 215/20; C07D 471/10; C07D 211/68; C07D 211/56
[52] U.S. Cl. .............. 546/16; 546/20; 546/194; 546/199; 546/215
[58] Field of Search .............. 546/16, 194, 199, 546/20, 215

[56] References Cited

U.S. PATENT DOCUMENTS

| | | | |
|---|---|---|---|
| 3,155,669 | 11/1964 | Janssen | 546/20 |
| 3,155,670 | 11/1964 | Janssen | 546/20 |
| 3,161,644 | 12/1964 | Janssen | 546/215 |
| 3,238,216 | 3/1966 | Janssen | 546/20 |
| 4,076,821 | 2/1978 | Tsuda et al. | 424/263 |
| 4,329,353 | 5/1982 | Stokbroekx et al. | 424/267 |

FOREIGN PATENT DOCUMENTS

| | | |
|---|---|---|
| 035902 | 9/1981 | European Pat. Off. . |
| 856 514 | 8/1998 | European Pat. Off. . |
| 2607300 | 9/1976 | Germany . |
| 100084/76 | 9/1976 | Japan . |
| 12171/77 | 1/1977 | Japan . |
| 5174/78 | 1/1978 | Japan . |
| 150086/81 | 11/1981 | Japan . |
| 139348/84 | 8/1984 | Japan . |

OTHER PUBLICATIONS

David Julius, Nature, 377, Oct. 12, p 476, 1995.
Ronald J. Mattson, et al., J. Org. Chem., 55, pp 2552–2554, 1990.
David M. Tschaen, et al., J. Org. Chem., 60, pp 4324–4330, 1995.
Yung–Chi Cheng, et al., Biochem. Pharmacol., 22, pp 3099–3108, 1973.
Triazaspirodecanone Der. C.A. # 102:6494 Rn # 61271–73–6p, Aug. 10, 1984.

*Primary Examiner*—Alan L. Rotman
*Assistant Examiner*—Rita Desai
*Attorney, Agent, or Firm*—George W. Johnston; Patricia S. Rocha-Tramaloni; Eileen M. Ebel

[57] ABSTRACT

The present invention relates to compounds of formula I and pharmaceutically acceptable acid addition salts thereof.

30 Claims, No Drawings

1,3,8,-TRIAZA SPIRO (4,5)DECAN-4-ON DERIVATIVES

BACKGROUND OF THE INVENTION

The present invention relates to compounds useful in treating disorders involving the Orphanin FQ receptor.

SUMMARY OF THE INVENTION

The present invention relates to compounds of the formula

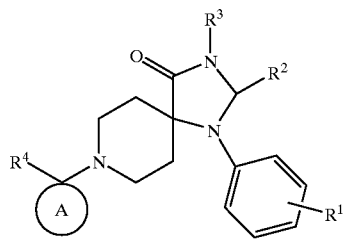

I wherein
- $R^1$ is hydrogen, lower alkyl, halogen, lower alkoxy, trifluoromethyl, lower alkyl-phenyl or $(C_{5-7})$-cycloalkyl;
- $R^2$ is hydrogen, lower alkyl, phenyl or lower alkyl-phenyl;
- $R^3$ is hydrogen, lower alkyl, benzyl, lower alkyl-phenyl, lower alkyl-diphenyl, triazinyl, cyanomethyl, lower alkyl-piperidinyl, lower alkyl-naphthyl, $(C_{5-7})$-cycloalkyl, lower alkyl-$(C_{5-7})$-cycloalkyl, lower alkyl-pyridinyl, lower alkyl-morpholinyl, lower alkyl-dioxolanyl, lower alkyl-oxazolyl or lower alkyl-2-oxo-oxazolidinyl, wherein the benzyl, phenyl, diphenyl, triazinyl, piperidinyl, naphthyl, $(C_{5-7})$-cycloalkyl, pyridinyl, morpholinyl, dioxolanyl, oxazolyl and oxazolidinyl rings are unsubstituted or are substituted by lower alkyl, lower alkoxy, trifluoromethyl or phenyl, or —$(CH_2)_nC(O)O$lower alkyl, —$(CH_2)_nC(O)NH_2$, —$(CH_2)_nC(O)N(\text{lower alkyl})_2$, —$(CH_2)_nOH$ or —$(CH_2)_nC(O)NHCH_2C_6H_5$;
- $R^4$ is a substituent at position 1 on A and is selected from hydrogen, lower alkyl or nitrilo;
- A is a ring system, consisting of
  - (a) $(C_{5-15})$-cycloalkyl, which is unsubstituted or substituted by lower alkyl, trifluoromethyl, phenyl, $(C_{5-7})$-cycloalkyl, spiro-undecan-alkyl or by 2-norbornyl, or is one of the following groups

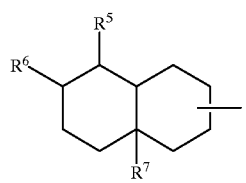

(b)

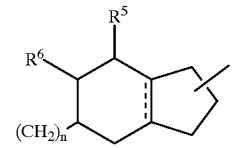

(c)

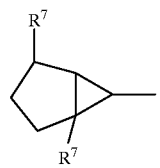

(d)

dodecahydro-acenaphthylen-1yl(e), bicyclo[6.2.0]dec-9-yl (f) and bicyclononan-9-yl (g);
and wherein
- $R^5$ and $R^6$ are hydrogen, lower alkyl or taken together and with the carbon atoms to which they are attached form a phenyl ring;
- $R^7$ is hydrogen or lower alkyl;
- the dotted line represents an optional bond and
- n is 1 to 4;
and pharmaceutically acceptable acid addition salts thereof.

The compounds of formula I and their salts are characterized by valuable therapeutic properties. It has surprisingly been found that the compounds of the present invention are agonists and/or antagonists of the Orphanin FQ (OFQ) receptor. Consequently they will be useful in the treatment of memory and attention deficits, psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of addictive drug withdrawal, control of water balance, $Na^+$ excretion, arterial blood pressure disorders and metabolic disorders such as obesity.

DETAILED DESCRIPTION OF THE INVENTION

The present invention relates to compounds of the formula

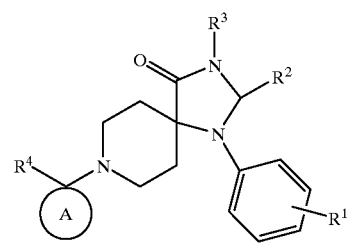

I wherein
- $R^1$ is hydrogen, lower alkyl, halogen, lower alkoxy, trifluoromethyl, lower alkyl-phenyl or $(C_{5-7})$-cycloalkyl;
- $R^2$ is hydrogen, lower alkyl, phenyl or lower alkyl-phenyl;

R³ is hydrogen, lower alkyl, benzyl, lower alkyl-phenyl, lower alkyl-diphenyl, triazinyl, cyanomethyl, lower alkyl-piperidinyl, lower alkyl-naphthyl, $(C_{5-7})$-cycloalkyl, lower alkyl-$(C_{5-7})$-cycloalkyl, lower alkyl-pyridinyl, lower alkyl-morpholinyl, lower alkyl-dioxolanyl, lower alkyl-oxazolyl or lower alkyl-2-oxo-oxazolidinyl, wherein the benzyl, phenyl, diphenyl, triazinyl, piperidinyl, naphthyl, $(C_{5-7})$-cycloalkyl, pyridinyl, morpholinyl, dioxolanyl, oxazolyl and oxazolidinyl rings are unsubstituted or are substituted by lower alkyl, lower alkoxy, trifluoromethyl or phenyl, or —$(CH_2)_nC(O)O$-lower alkyl, —$(CH_2)_nC(O)NH_2$, —$(CH_2)_nC(O)N(\text{lower alkyl})_2$, —$(CH_2)_nOH$ or —$(CH_2)_nC(O)NHCH_2C_6H_5$;

$R^4$ is a substituent at position 1 on A and is selected from hydrogen, lower alkyl or nitrilo;

A is a ring system selected from
(a) $(C_{5-15})$-cycloalkyl, which is unsubstituted or substituted by lower alkyl, trifluoromethyl, phenyl, $(C_{5-7})$-cycloalkyl, spiro-undecan-alkyl or by 2-norbornyl, or is one of the following groups (b)

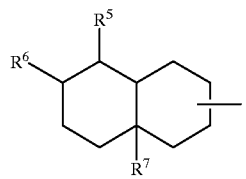

(c)

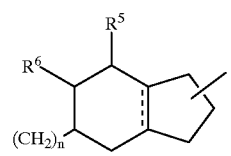

(d)

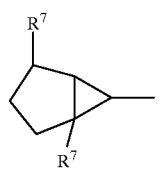

dodecahydro-acenaphthylen-1yl (e), bicyclo[6.2.0]dec-9-yl (f) and bicyclononan-9-yl (g);
and wherein
$R^5$ and $R^6$ are hydrogen, lower alkyl or taken together with the carbon atoms to which they are attached form a phenyl ring;
$R^7$ is hydrogen or lower alkyl;
the dotted line represents an optional bond and
n is 1 to 4;
and to pharmaceutically acceptable acid addition salts thereof.

The compounds of formula I and their salts are characterized by valuable therapeutic properties. It has surprisingly been found that the compounds of the present invention are agonists and/or antagonists of the Orphanin FQ (OFQ) receptor. Consequently they will be useful in the treatment of memory and attention deficits, psychiatric, neurological and physiological disorders, especially, but not limited to, amelioration of symptoms of anxiety and stress disorders, depression, trauma, memory loss due to Alzheimer's disease or other dementias, epilepsy and convulsions, acute and/or chronic pain conditions, symptoms of addictive drug withdrawal, control of water balance, Na+ excretion, arterial blood pressure disorders and metabolic disorders such as obesity.

OFQ, a seventeen amino-acid-long peptide (F-G-G-F-T-G-A-R-K-S-A-R-K-L-A-N-Q), has been isolated from rat brain and is a natural ligand to a G-protein coupled receptor (OFQ-R), found at high levels in brain tissue.

OFQ exhibits agonistic action at the OFQ-R both in vitro and in vivo.

Julius (Nature 377,476, [1995]) discusses the discovery of OFQ noting that this peptide shares greatest sequence similarity with dynorphin A, an established endogenous ligand for opioid receptors. OFQ inhibits adenylate cyclase in CHO(LC 132⁺) cells in culture and induces hyperalgesia when administered intra-cerebroventricularly to mice. The pattern of results indicate that this heptadecapeptide is an endogenous agonist of the LC 132 receptor and it appears to have pro-nociceptive properties. It was described that when injected intra-cerebroventricularly in mice, OFQ slowed down locomotive activity and induced hyperalgesia. It was concluded that OFQ may act as a brain neurotransmitter to modulate nociceptive and locomotive behavior.

Objects of the present invention are the compounds of formula I and pharmaceutically acceptable addition salts thereof, racemic mixtures and their corresponding enantiomers, the preparation of the above-mentioned compounds, medicaments containing them and their manufacture as well as the use of the above-mentioned compounds in the control or prevention of illnesses, especially of illnesses and disorders of the kind referred to earlier, or in the manufacture of corresponding medicaments.

The following definitions of the general terms used in the present description apply irrespective of whether the terms in question appear alone or in combination.

As used herein, the term "lower alkyl" denotes a straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group containing from 5–15 carbon atoms, preferred are cyclohexyl, cyclodecyl and cyclononyl.

The term "halogen" denotes chlorine, iodine, fluorine and bromine.

The term "lower alkoxy" denotes a group wherein the alkyl residues is as defined above, and which is attached via an oxygen atom.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Exemplary preferred are compounds, in which A is a unsubstituted decahydro-naphthalen group (formula b) and $R^1$–$R^3$ are hydrogen or $R^3$ is methyl and $R^1$ and $R^2$ are hydrogen, for example the following compounds:

8-(Decahydro-naphthalen-2-yl)-1-phenyl-1,3,8-triaza-spiro[4.5]decan-4-one, 8-(Decahydro-naphthalen-2-yl)-3-methyl-1-phenyl-1,3,8-triaza-spiro[4.5]decan-4-one, mixture of (2RS,4aRS,8aSR)- and (2SR,4aRS,8aSR)-8-(decahydro-naphthalen-2-yl)-1-phenyl-1,3,8-triaza-spiro[4.5]decan-4-one or (2RS,4aSR,8aRS)-8-(Decahydro-naphthalen-2-yl)-1-phenyl-1,3,8-triaza-spiro[4.5]decan-4-one.

Further preferred are compounds, in which A is cyclohexyl, optionally substituted by methyl or isopropyl, cyclodecyl or cyclononyl (formula a) and $R^1$–$R^3$ are hydrogen.

Examples of such compounds are cis-8-(4-Methyl-cyclohexyl)-1-phenyl-1,3,8-triaza-spiro[4.5]decan-4-one, 8-Cyclodecyl-1-phenyl-1,3,8-triaza-spiro[4.5]decan-4-one 8-Cyclononyl-1-phenyl-1,3,8-triaza-spiro[4.5]decan-4-one or cis-8-(4-Isopropyl-cyclohexyl)-1-phenyl-1,3,8-triaza-spiro[4.5]decan-4-one.

Preferred are further compounds, in which A is cyclodecyl, (formula a) and $R^1$ is hydrogen or methyl, $R^2$ is hydrogen or phenyl and $R^3$ is hydrogen or acetonitrile.

Examples of such compounds are (R,S)-8-Cyclodecyl-1-(3-methyl-phenyl)-2-phenyl-1,3,8-triaza-spiro[4,5]decan-4-one or 8-Cyclodecyl-4-oxo-1-phenyl-1,3,8-triaza-spiro[4,5]dec-3-yl)-acetonitrile.

Further preferred are compounds, in which A is octahydro-inden (formula c) and $R^1$–$R^3$ are hydrogen, for example the following compound:

8-(cis-Octahydro-inden-2-yl)-1-phenyl-1,3,8-triaza-spiro[4,5]decan-4-one.

Further preferred is the following compound:

8-(cis-Bicyclo[6.2.0]dec-9-yl)-1-phenyl-1,3,8-triaza-spiro[4,5]decan-4-one.

The present compounds of formula I and their pharmaceutically acceptable salts can be prepared by methods known in the art, for example, by processes described below, which comprise a) reductively aminating a compound of formula

II with a compound of formula

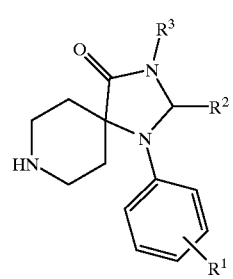

III or, if desired, adding KCN to the mixture of a compound of formula II and III to get a compound of formula I, wherein $R^4$ is hydrogen or nitrilo, respectively, and wherein A and $R^1$–$R^3$ have the significances given above, or b) cyclizing and reducing a compound of formula

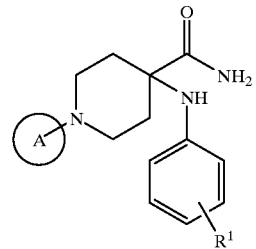

IV to give a compound of formula

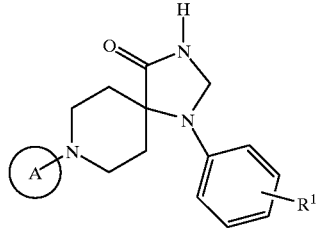

I-1 wherein A and $R^1$ have the significances given above, or c) reacting a compound of formula

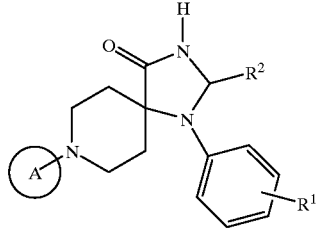

I-3 with a compound of formula $R^3X$ wherein $R^3$ is described as above, but different from hydrogen and X is halogen, to give a compound of formula

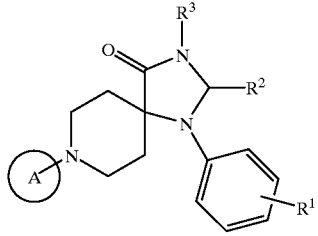

I-2 or d) alkylating or benzylating a compound of formula I, wherein $R^3$ is hydrogen, and, if desired, e) converting a racemic mixture into its enantiomeric component thus obtaining optically pure compounds, and/or, if desired, f) converting the compound of formula I obtained into a pharmaceutically acceptable acid addition salt.

g) In accordance with process variant a) the reductive amination of a keto compound of formula II with an amine of formula III is carried out in conventional manner in a solvent, such as toluene, tetrahydrofuran (THF), methanol or ethanol, or in a mixture of THF with a suitable alcohol, and in the present of a reducing agent such as Na-cyanoborhydride, or in the presence of KCN, respectively.

Another method for a reductive amination is described in J. Org. Chem., 55, 2552–54, 1990. In accordance with this variant the reaction is carried out by reaction of an amine with a ketone in the presence of TI-(IV)-isopropoxide and Na-cyanoborohyride.

The cyclisation in accordance with process step b) can be carried out in conventional manner, for example with formamide at a temperature of about 200° C. or with formic acid ortho esters at a temperature of about 150° C. Unsaturated products can be converted to the saturated compounds by reduction, for example with sodium cyanoborohydride.

A compound of formula I can further be prepared by reacting a compound of formula I-1 with a compound of formula $R^3X$ in accordance with reaction step c). This reaction is carried out in a suitable solvent, such as DMF, and in the presence of sodium hydride at room temperature. Suitable halogenides of formula $R_3X$ are chlorides, bromides and iodides, such as methyl iodide, bromomethyl acetate, N,N-dimethyl-chloroacetamide or ethyl-5-bromovaleriate. The reaction time is about 18 h.

In accordance with process variant d) a compound of formula I, wherein $R^3$ is hydrogen, can be alkylated or benzylated in conventional manner, for example in the presence of a corresponding alkyl- or benzyl halogenide, such as methyliodide, ethyliodide, benzylbromide, 3-phenyl-1-propylbromide or 3,3-diphenyl-1-propylbromide. This reaction is carried out in the presence of a metal hydride, such as sodium hydride at a temperature of about 60–100° C.

Racemic mixtures can be converted into its enantiomeric components in conventional manner, for example by preparative HPLC.

The salt formation in accordance with variant f) is effected at room temperatures in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methanesulphonates, p-toluenesulfonates and the like are examples of such salts.

The compounds of formulae II and III which are used as starting materials are known compounds or can be prepared by methods known per se.

For example, the ketones of formula II can be prepared by methods, described in Beilstein H7, EI7, EII7, EIII7 and EIV7. Compounds of formula III are described, for example, in U.S. Pat. No. 3,238,216, U.S. Pat. No. 3,161,644, U.S. Pat. No. 3,155,670 and U.S. Pat. No. 3,155,669.

Schemes 1 and 4 describe the reductive amination in accordance with process variant a).

Scheme 1

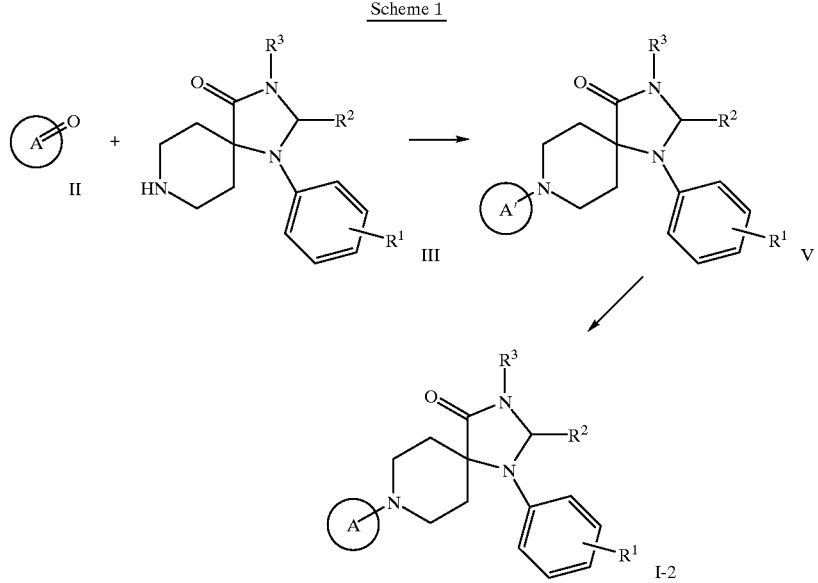

wherein A' is a compound of group A having a partially unsaturated ring (one double bond) and A and $R^1$–$R^3$ have the significances given above.

Scheme 2 shows a process for the preparation of compounds of formula I-1.

Scheme 2

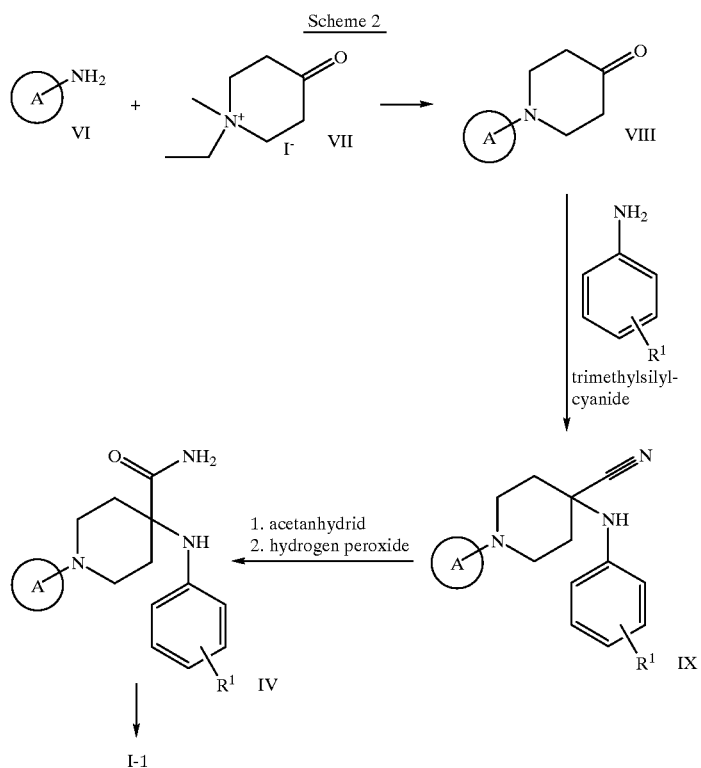

$R^1$ and A have the significances given above.

The starting materials of formulae VI and VII are known compounds or can be prepared according to methods known in the art, for example compounds of formula VI can be prepared in accordance with Beilstein H12, EI12, EII12, EIII12 and EIV12. Compounds of formula VII can be prepared by methods described in Tschaen et al., J.Org.Chem., 60, 4324 (1995).

In scheme 3 it is described the cyclization of compounds of formula IV to a compound of formula X and then to a compound of formula I-2. In this scheme the substituents are as described above. The starting materials of formula IV are known compounds or can be prepared by methods known in the art.

Scheme 3

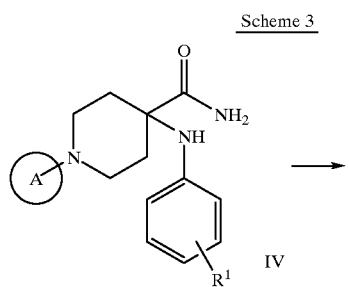

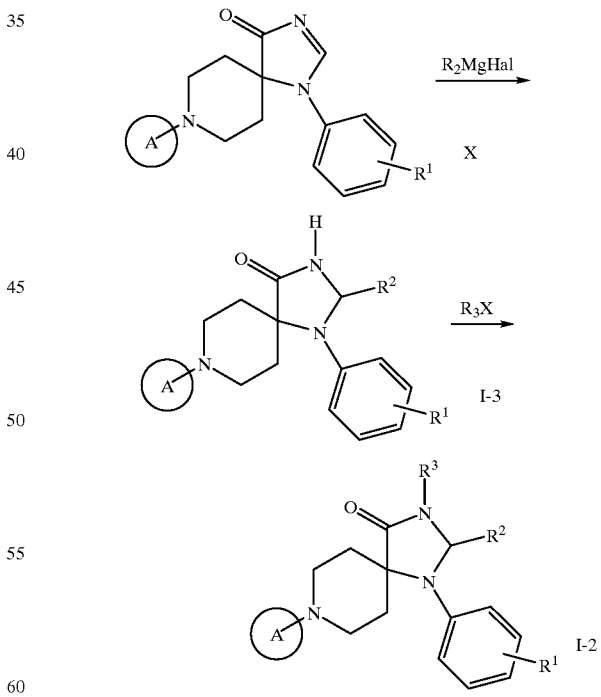

In the following scheme 4 is described the process for preparation of compounds of formula I, wherein A is cyclohexyl, optionally substituted by lower alkyl, $C_{5-7}$-cycloalkyl, spiro-undecan-alkyl or 2-norbonyl and $R^4$ in this scheme is lower alkyl.

Scheme 4

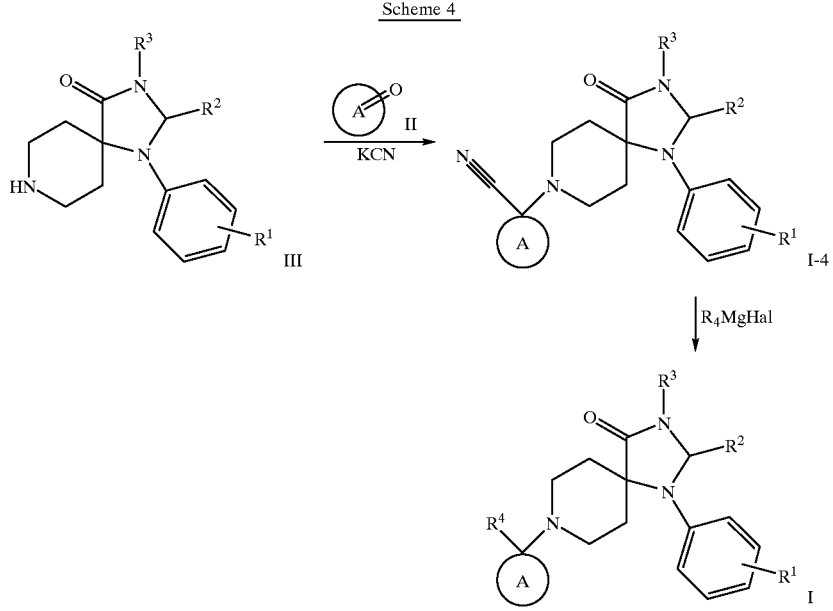

As mentioned earlier, the compounds of formula I and their pharmaceutically usuable addition salts possess valuable pharmacodynamic properties. It has been found that the compounds of the present invention are agonists and/or antagonists of the OFQ receptor and have effects in animal models of psychiatric, neurological and physiological disorders, such as anxiety, stress disorders, depression, trauma, memory loss due to Alzheimer's disease or other dementias, epilepsy and convulsions, acute and/or chronic pain conditions, symptoms of addictive drug withdrawal, control of water balance, Na+ excretion, arterial blood pressure disorders and metabolic disorders such as obesity.

The compounds were investigated in accordance with the tests given hereinafter:

Methods of OFQ-R Binding Assay
Cell Culture

HEK-293 cells adapted to suspension growth (293s) were cultured in HL medium plus 2% FBS. The cells were transfected with the rat OFQ receptor cDNA (LC132), FEBS Lett. 347, 284–288,1994, cloned in the expression vector pCEP4 (Invitrogen, SanDiego, Calif., USA) using lipofectin (Life Technologies, Bethesda, Md., USA). Transfected cells were selected in the presence of hygromycin (1000 U/ml) (Calbiochem, SanDiego, Calif., USA). A pool of resistant cells was tested for OFQ-R expression by binding of [$^3$H]-OFQ (Amersham PLC, Buckinghamshire, England). These cells (293s-OFQ-R) were expanded for large scale culture and membrane preparation.

Membrane preparation

293s-OFQ-R cells were harvested by centrifugation, washed 3 times with phosphate buffered saline (PBS) before resuspension in buffer A (50 mM Tris-HCl, pH 7.8, 5 mM MgCl2, 1 mM EGTA) and disruption with a tissue homogenizer (30 seconds, setting 4, Pt 20, Kinematica, Kriens-Lucern, Switzerland). A total membrane fraction was obtained by centrifugation at 49,000×g at 4° C. This procedure was repeated twice and the pellet was resuspended in buffer A. Aliquots were stored at −70° C. and protein concentrations were determined using the BCA™ Protein Assay Reagent (Pierce, Rockford, Ill.) following the manufacturer's recommendations.

Binding Assays [$^3$H]-OFQ competition studies were carried out with 77 μg membrane protein in a final assay volume of 0.5 ml buffer A plus 0.1% BSA and 0.01% bacitracin (Boehringer-Mannheim, Mannheim, Germany) for one hour at room temperature. 50 nM unlabeled OFQ was used to define the non-specific binding. The assays were terminated by filtration through Whatman GF/C filters (Unifilter-96, Canberra Packard S.A., Zurich, Switzerland) pretreated with 0.3% polyethylenimine (Sigma, St. Louis, Mo., USA) and 0.1% BSA (Sigma) for 1 hour. The filters were washed 6 times with 1 ml of ice bold 50 mM Tris-HCl pH 7.5. The retained radioactivity was counted on a Packard Top-Count microplate scintillation counter after addition of 40 μl of Microscint 40 (Canberra Packard). The effects of compounds were determined using at least 6 concentrations in triplicate, and determined twice. IC50 values were determined by curve fitting and these calues were converted to $K_i$ values by the method of Cheng and Prusoff, Biochem. Pharmacol., 22, 3099, 1973.

The affinity to the OFQ-receptor, given as $pK_i$, is in the scope of 6,2 to 10,0. For example, the $pK_i$-values of Examples 16 and 24 are 8,4 and 9,5, respectively.

Example 16, Mixture of cis- and trans-1-phenyl-8-(4-propyl-cyclohexyl)-1,3,8-triaza-spiro[4,5]decan-4-one Example 24, 8-(Decahydro-naphthalen-2-yl)-3-methyl-1-phenyl-1,3,8-triaza-spiro-[4,5]decan-4-one The compounds of formula I as well as their pharmaceutically usable acid addition salts can be used as medicaments, e.g. in the form of pharmaceutical preparations. The pharmaceutical preparations can be administered orally, e.g. in the form of tablets, coated tablets, dragées, hard and soft gelatine capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragées and hard gelatine capsules.

Lactose, corn starch or derivatives thereof, talc, stearic acid or its salts etc can be used as such excipients e.g. for tablets, dragées and hard gelatine capsules.

Suitable excipients for soft gelatine capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

The following Examples illustrate the present invention without limiting it. All temperatures are given in degrees Celsius.

EXAMPLE 1

8-Cyclohexyl-1-phenyl-1,3,8-triaza-spiro[4,5]decan-4-one hydrochloride (1:1)

Cyclohexanone (4.3 mmol) was dissolved in toluene (50 ml). 1-Phenyl-1,3,8-triazaspiro[4,5]decan-4-one (4.3 mmol) and molecular sieves (3.3 g) were added and the mixture was refluxed for 18 h. After cooling the molecular sieves were removed by filtration and washed with methylenchloride. Evaporation of the filtrate yielded a residue which was dissolved in THF (45 ml) and ethanol (5 ml). Sodium cyanoborohydride (4.3 mmol) was added to the solution and the pH was adjusted to 4. The mixture was stirred for 3 h at room temperature. Water and ethylacetate was added and the organic phase was washed with 2 N sodium hydroxide and brine. The organic phase was dried with $Na_2SO_4$ and concentrated. Chromatography on silica gel (methylenchloride/methanol, 98:2) yielded the desired product which was crystallized as its HCl-salt from ethylacetate/methanol. 0.96 g (64%) 8-cyclohexyl-1-phenyl-1,3,8-triaza-spiro[4,5]decan-4-one hydrochloride (1:1) as a colorless solid, m.p.>250° C. and MS: m/e=313 ($M^+$).

EXAMPLE 2 cis-8-(4-tert-Butyl-cyclohexyl)-1-phenyl-1,3,8-triaza-spiro[4,5]decan-4-one hydrochloride (1:1)

The title compound, m.p.>250° C. and MS: m/e=370 ($M+H^+$) was prepared in accordance with the general method of example 1 from 4-(1,1-dimethylethyl)-cyclohexanone and 1-phenyl-1,3,8-triazaspiro[4,5]decan-4-one.

EXAMPLE 3 cis-1-Phenyl-8-(4-phenyl-cyclohexyl)-1,3,8-triaza-spiro[4,5]decan-4-one hydrochloride (1:1)

The title compound, m.p.>250° C. and MS: m/e=390 ($M+H^+$) was prepared in accordance with the general method of example 1 from 4-phenyl-cyclohexanone and 1-phenyl-1,3,8-triazaspiro[4,5]decan-4-one.

EXAMPLE 4

Mixture of (1RS,3RS)- and (1RS,3SR)-8-(3-methyl-cyclohexyl)-1-phenyl-1,3,8-triaza-spiro[4,5]decan-4-one hydrochloride (1:1)

The title compound, m.p.>250° C. and MS: m/e=328 ($M+H^+$) was prepared in accordance with the general method of example 1 from 3-methyl-cyclohexanone and 1-phenyl-1,3,8-triazaspiro[4,5]decan-4-one.

EXAMPLE 5

Mixture of cis- and trans-8-(4-methyl-cyclohexyl)-1-phenyl-1,3,8-triaza-spiro[4,5]decan-4-one hydrochloride (1:1)

The title compound, m.p.>250° C. and MS: m/e=328 ($M+H^+$) was prepared in accordance with the general method of example 1 from 4-methyl-cyclohexanone and 1-phenyl-1,3,8-triazaspiro[4,5]decan-4-one.

EXAMPLE 6 trans-8-(4-tert-Butyl-cyclohexyl)-1-phenyl-1,3,8-triaza-spiro[4,5]decan-4-one hydrochloride (1:1)

The title compound, m.p.>250° C. and MS: m/e=370 ($M+H^+$) was prepared in accordance with the general method of example 1 from 4-(1,1-dimethylethyl)-cyclohexanone and 1-phenyl-1,3,8-triazaspiro[4,5]decan-4-one.

EXAMPLE 7

1-Phenyl-8-(3,3,5,5-tetramethyl-cyclohexl)-1,3,8-triaza-spiro[4,5]decan-4-one hydrochloride (1:1)

The title compound, m.p.>250° C. and MS: m/e=370 ($M+H^+$) was prepared in accordance with the general method of example 1 from 3,3,5,5-tetramethyl-cyclohexanone and 1-phenyl-1,3,8-triazaspiro[4,5]decan-4-one.

EXAMPLE 8

Mixture of (1RS,2RS)- and (1RS,2SR)-8-(2-methyl-cyclohexnl)-1-phenyl-1,3,8-triaza-spiro[4,5]decan-4-one hydrochloride (1:1)

2-Methyl-cyclohexanone (4.5 mmol) was dissolved in THF (10 ml). 1-Phenyl-1,3,8-triazaspiro[4,5]decan-4-one (4.5 mmol) and tetraisopropyl-orthotitanate (4.5 mmol) were added and the mixture was stirred for 18 h at room temperature. Evaporation yielded a residue which was dissolved in ethanol (7 ml). Sodium cyanoborohydride (4.3 mmol) was added to the solution and the mixture was stirred for 18 h at room temperature. Water and ethylacetate was added and the organic phase was washed with 2 N sodium hydroxide and brine. The organic phase was dried with $Na_2SO_4$ and concentrated. Chromatography on silica gel (dichloromethane/methanol, 98:2) yielded the desired product which was crystallized as its HCl-salt from ethylacetate/ethanol. 0.34 g (21%) of a mixture of (1RS,2RS)- and (1RS,2SR)-8-(2-methyl-cyclohexyl)-1-phenyl-1,3,8-triaza-spiro[4,5]decan-4-one hydrochloride (1:1) as a colorless solid, m.p.>250° C. and MS: m/e=327 ($M^+$).

EXAMPLE 9

8-(Decahydro-naphthalen-2-yl)-1-phenyl-1,3,8-triaza-spiro[4,5]decan-4-one hydrochloride (1:1) (mixture of the diast. racemates)

The title compound, m.p.>250° C. and MS: m/e=368 (M+H$^+$) was prepared in accordance with the general method of example 1 from octahydro-2(1H)-naphthalenone and 1-phenyl-1,3,8-triazaspiro[4,5]decan-4-one.

EXAMPLE 10

Mixture of (1R,3R)- and (1S,3R)-8-(3-methyl-cyclohexyl)-1-phenyl-1,3,8-triaza-spiro[4,5]decan-4-one hydrochloride (1:1)

The title compound, m.p.>250° C. and MS: m/e=328 (M+H$^+$) was prepared in accordance with the general method of example 1 from (R)-3-methyl-cyclohexanone and 1-phenyl-1,3,8-triazaspiro[4,5]decan-4-one.

EXAMPLE 11

Mixture of (1RS,4aRS,8aSR)- and (1SR,4aRS,8aSR)-

8-(Decahydro-naphthalen-1-yl)-1-phenyl-1,3,8-triaza-spiro[4,5]decan-4-one hydrochloride (1:1)

The title compound, m.p.>250° C. and MS: m/e=367 (M$^+$) was prepared in accordance with the general method of example 8 from trans-octahydro-2(1H)-naphthalenone and 1-phenyl-1,3,8-triazaspiro[4,5]decan-4-one.

EXAMPLE 12

Mixture of (1RS,3RS)- and (1RS,3SR)-8-(3-tert-butyl-cyclohexyl)-1-phenyl-1,3,8-triaza-spiro[4,5]decan-4-one hydrochloride (1:1)

The title compound, m.p.>250° C. and MS: m/e=369 (M$^+$) was prepared in accordance with the general method of example 1 from 3-(1,1-dimethylethyl)-cyclohexanone and 1-phenyl-1,3,8-triazaspiro[4,5]decan-4-one.

EXAMPLE 13

(1RS,3RS)-1-Phenyl-8-(3-phenyl-cyclohexyl)-1,3,8-triaza-spiro[4,5]decan-4-one hydrochloride (1:1)

The title compound, m.p.>250° C. and MS: m/e=389 (M$^+$) was prepared in accordance with the general method of example 1 from 3-phenyl-cyclohexanone and 1-phenyl-1,3, 8-triazaspiro[4,5]decan-4-one.

EXAMPLE 14

Mixture of (1RS,5RS)- and (1RS,5SR)-1-phenyl-8-(3,3,5-trimethyl-cyclohexyl)-1,3,8-triaza-spiro[4,5]decan-4-one hydrochloride (1:1)

The title compound, m.p.>250° C. and MS: m/e=355 (M$^+$) was prepared in accordance with the general method of example 1 from 3,3,5-trimethyl-cyclohexanone and 1-phenyl-1,3,8-triazaspiro[4,5]decan-4-one.

EXAMPLE 15

(1RS,3SR)-1-Phenyl-8-(3-phenyl-cyclohexyl)-1,3,8-triaza-spiro[4,5]decan-4-one hydrochloride (1:1)

The title compound, m.p.>250° C. and MS: m/e=389 (M$^+$) was prepared in accordance with the general method of example 1 from 3-phenyl-cyclohexanone and 1-phenyl-1,3, 8-triazaspiro[4,5]decan-4-one.

EXAMPLE 16

Mixture of cis- and trans 1-phenyl-8-(4-prolyl-cyclohexyl)-1,3,8-triaza-spiro[4,5]decan-4-one hydrochloride (1:1)

The title compound, m.p.>250° C. and MS: m/e=356 (M+H$^+$) was prepared in accordance with the general method of example 1 from 4-propyl-cyclohexanone and 1-phenyl-1,3,8-triazaspiro[4,5]decan-4-one.

EXAMPLE 17

1:1 Mixture of (2R,4aS,8aR)- and (2S,4aS,8aR)-8-(4a-methyl-decahydro-naphthalen-2-yl)-1-phenyl-1,3,8-triaza-spiro[4,5]decan-4-one hydrochloride (1:1)

The title compound, m.p.>250° C. and MS: m/e=382 (M+H$^+$) was prepared in accordance with the general method of example 1 from (4aS-cis)-octahydro-4a-methyl-2(1H)-naphthalenone and 1-phenyl-1,3,8-triazaspiro[4,5]decan-4-one.

EXAMPLE 18

1:1 Mixture of (2R,4aR,8aS)- and (2S,4aR,8aS)-8-(4a-methyl-decahydro-naphthalen-2-yl)-1-phenyl-1,3,8-triaza-spiro[4,5]decan-4-one hydrochloride (1:1)

The title compound, m.p.>250° C. and MS: m/e=382 (M+H$^+$) was prepared in accordance with the general method of example 1 from (4aR-cis)-octahydro-4a-methyl-2(1H)-naphthalenone and 1-phenyl-1,3,8-triazaspiro[4,5]decan-4-one.

EXAMPLE 19

(2S,4aR,8aS)-8-(4a-Methyl-decahydro-naphthalen-2-yl)-1-phenyl-1,3,8-triaza-spiro[4,5]decan-4-one The title compound, NMR (CDCl$_3$): 0.96 (s, 3H), 1.8–1.0 (m, 17 H), 2.4 (m, 1H), 2.62 (m, 2H), 2.85 (m, 2H), 3.05 (t, 2H), 4.72 (s, 2H), 6.46 (bs, 1H), 6.89 (m, 3H), 7.27 (t, 2H) was isolated by preparative HPLC of the mixture obtained in example 18.

EXAMPLE 20

(2R,4aR,8aS)-8-(4a-Methyl-decahydro-naphthalen-2-yl)-1-phenyl-1,3,8-triaza-spiro[4,5]decan-4-one The title compound, NMR (CDCl$_3$): 0.97 (s, 3H), 1.8–1.0 (m, 17 H), 2.58 (m, 3H), 2.84 (m, 2H), 3.02 (m, 2H), 4.72 (s, 2H), 6.40 (bs, 1H), 6.92 (m, 3H), 7.27 (t, 2H) was isolated by preparative HPLC of the mixture obtained in example 18.

EXAMPLE 21

(2S,4aS,8aR)-8-(4a-Methyl-decahydro-naphthalen-2-yl)-1-phenyl-1,3,8-triaza-spiro[4,5]decan-4-one The title compound, NMR (CDCl$_3$): 0.97 (s, 3H), 1.8–1.0 (m, 17 H), 2.4 (m, 1H), 2.60 (m, 2H), 2.83 (m, 2H), 3.05 (t, 2H), 4.73 (s, 2H), 6.58 (bs, 1H), 6.87 (t, 1H), 6.94 (d, 2H), 7.27 (t, 2H) was isolated by preparative HPLC of the mixture obtained in example 17.

EXAMPLE 22

1:1 Mixture of (2R,4aS,8aS)- and (2S,4aS,8aS)-8-(4a-methyl-decahydro-naphthalen-2-yl)-1-phenyl-1,3,8-triaza-spiro[4,5]decan-4-one hydrochloride (1:1)

The title compound, m.p.>250° C. and MS: m/e=382 (M+H$^+$) was prepared in accordance with the general

EXAMPLE 23

1:1 Mixture of (2R,4aR,8aR)- and (2R,4aR,8aR)-8-(4a-methyl-decahydro-naphthalen-2-yl)-1-phenyl-1,3,8-triaza-spiro[4,5]decan-4-one hydrochloride (1:1)

The title compound, m.p.>250° C. and MS: m/e=382 (M+H$^+$) was prepared in accordance with the general method of example 1 from (4aR-trans)-octahydro-4a-methyl-2(1H)-naphthalenone and 1-phenyl-1,3,8-triazaspiro[4,5]decan-4-one.

EXAMPLE 24

8-(Decahydro-naphthalen-2-yl)-3-methyl-1-phenyl-1,3,8-triaza-spiro[4,5]decan-4-one hydrochloride (1:1) (mixture of the diast. racemates)

8-(Decahydro-naphthalen-2-yl)-1-phenyl-1,3,8-triaza-spiro[4,5]decan-4-one hydrochloride (1:1) (1.2 mmol) was suspended in DMF (20 ml). Sodium hydride (2.4 mmol) was added and the mixture was stirred at 80° C. for 1 h. The mixture was cooled to room temperature, methyl iodide (1.2 mmol) was added and the mixture was stirred for 18 h. DMF was evaporated, sodium bicarbonate and ethylacetate were added. The organic phase was washed with brine, dried with MgSO$_4$ and concentrated. Chromatography on silica gel (methylenchloride/methanol, 98:2) yielded the desired product which was crystallized as its HCl-salt from ethylacetate/ethanol. 0.19 g (36%) 8-(decahydro-naphthalen-2-yl)-3-methyl-1-phenyl-1,3,8-triaza-spiro[4,5]decan-4-one hydrochloride (1:1) as a colorless solid, m.p.>250° C. and MS: m/e=382 (M+H$^+$).

EXAMPLE 25 cis-8-(4-Methyl-cyclohexyl)-1-phenyl-1,3,8-triaza-spiro[4,5]decan-4-one hydrochloride (1:1)

The title compound, m.p.>250° C. and NMR (DMSO-d$_6$): 0.96 (d, 3H), 1.9–1.5 (m, 11H), 2.99 (t, 2H), 3.16 (m, 1H), 3.43 (m, 2H), 3.66 (m, 2H), 4.62 (s, 2H), 6.97 (t, 1H), 7.08 (d, 2H), 7.22 (t, 2H), 9.02 (s, 1H), 10.35 (bs, 1H) was isolated by preparative HPLC of the mixture obtained in example 5.

EXAMPLE 26 trans-8-(4-Methyl-cyclohexyl)-1-phenyl-1,3,8-triaza-spiro[4,5]decan-4-one hydrochloride (1:1)

The title compound, m.p.>250° C. and NMR (DMSO-d$_6$): 0.87 (d, 3H), 0.97 (t, 2H), 1.3 (m, 1H), 1.54 (m, 2H), 1.90 (t, 2H), 2.08 (d, 2H), 2.97 (t, 2H), 3.16 (m, 1H), 3.4 (m, 2H), 3.70 (m, 2H), 4.62 (s, 2H), 6.81 (t, 1H), 7.08 (d, 2H), 7.22 (t, 2H), 9.02 (s, 1H), 10.35 (bs, 1H) was isolated by preparative HPLC of the mixture obtained in example 24.

EXAMPLE 27 cis-8-[4-(1,1-Dimethyl-propyl)-cyclohexyl]-1-phenyl-1,3,8-triaza-spiro[4,5]decan-4-one hydrochloride (1:1)

The title compound, m.p.>250° C. and MS: m/e=384 (M+H$^+$) was prepared in accordance with the general method of example 1 from 4-(1,1-dimethylpropyl)-cyclohexanone and 1-phenyl-1,3,8-triazaspiro[4,5]decan-4-one.

EXAMPLE 28 trans-8-[4-(1,1-Dimethyl-propyl)-cyclohexyl]-1-lphenyl-1,3,8-triaza-spiro[4,5]decan-4-one hydrochloride (1:1)

The title compound, m.p.>250° C. and MS: m/e=384 (M+H$^+$) was prepared in accordance with the general method of example 1 from 4-(1,1-dimethylpropyl)-cyclohexanone and 1-phenyl-1,3,8-triazaspiro[4,5]decan-4-one.

EXAMPLE 29

Mixture of (2RS,4aRS,8aSR)- and (2SR,4aRS,8aSR)-8-(decahydro-nalhthalen-2-yl-1-phenyl-1,3,8-triaza-spiro[4,5]decan-4-one hydrochloride (1:1)

The title compound, m.p.>250° C. and MS: m/e=368 (M+H$^+$) was prepared in accordance with the general method of example 1 from cis-octahydro-2(1H)-naphthalenone and 1-phenyl-1,3,8-triazaspiro[4,5]decan-4-one.

EXAMPLE 30

Mixture of cis- and trans 8-(4-Cyclohexyl-cyclohexyl)-1-phenyl-1,3,8-triaza-spiro[4,5]decan-4-one hydrochloride (1:1)

The title compound, m.p.>250° C. and MS: m/e=356.3 (M+H$^+$) was prepared in accordance with the general method of example 1 from 4-cyclohexylcyclohexanone and 1-phenyl-1,3,8-triazaspiro[4,5]decan-4-one.

EXAMPLE 31

Mixture of cis- and trans 8-(4-Isopropyl-cyclohexyl)-1-phenyl-1,3,8-triaza-spiro[4,5]decan-4-one hydrochloride (1:1)

The title compound, m.p.>250° C. and MS: m/e=384 (M+H$^+$) was prepared in accordance with the general method of example 1 from 4-isopropylcyclo-hexanone and 1-phenyl-1,3,8-triazaspiro[4,5]decan-4-one.

EXAMPLE 32

8-Cyclododecyl-1-phenyl-1,3,8-triaza-spiro[4,5]decan-4-one hydrochloride (1:1)

The title compound, white solid, m.p.>230° C. and MS: m/e=398.4 (M+H$^+$) was prepared in accordance with the general method of example 1 from cyclododecanone and 1-phenyl-1,3,8-triazaspiro[4,5]decan-4-one.

EXAMPLE 33

8-[2-(2-norbornyl)-cyclopentyl]-1-phenyl-1,3,8-triaza-spiro[4,5]decan-4-one hydrochloride (1:1) (mixture of diastereoisomers)

The title compound, white solid, m.p.>230° C. and MS: m/e=394.3 (M+H$^+$) was prepared in accordance with the general method of example 8 from rac-2-(2-norbornyl)-cyclopentanone and 1-phenyl-1,3,8-triazaspiro[4,5]decan-4-one.

EXAMPLE 34

8-Cyclodecyl-1-phenyl-1,3,8-triaza-spiro[4,5]decan-4-one hydrochloride (1:1)

The title compound, white solid, m.p.>220° C. and MS: m/e=370.3 (M+H⁺) was prepared in accordance with the general method of example 1 from cyclodecanone and 1-phenyl-1,3,8-triazaspiro[4,5]decan-4-one.

EXAMPLE 35

8-Cycloheptyl-1-phenyl-1,3,8-triaza-spiro[4,5]decan-4-one hydrochloride (1:1)

The title compound, white solid, m.p.>230° C. and MS: m/e=328.3 (M+H⁺) was prepared in accordance with the general method of example 1 from cycloheptanone and 1-phenyl-1,3,8-triazaspiro[4,5]decan-4-one.

EXAMPLE 36

8-Cyclooctyl-1-phenyl-1,3,8-triaza-spiro[4,5]decan-4-one hydrochloride (1:1)

The title compound, white solid, m.p.>230° C. and MS: m/e=328.3 (M+H⁺) was prepared in accordance with the general method of example 1 from cyclooctanone and 1-phenyl-1,3,8-triazaspiro[4,5]decan-4-one.

EXAMPLE 37

Cyclononyl-1-phenyl-1,3,8-triaza-spiro[4,5]decan-4-one hydrochloride (1:1)

The title compound, white solid, m.p.>220° C. and MS: m/e=356.3 (M+H⁺) was prepared in accordance with the general method of example 1 from cyclononanone and 1-phenyl-1,3,8-triazaspiro[4,5]decan-4-one.

EXAMPLE 38

8-Cycloundecyl-1-phenyl-1,3,8-triaza-spiro[4,5]decan-4-one hydrochloride (1:1)

The title compound, white solid, m.p.>220° C. and MS: m/e=384.3 (M+H⁺) was prepared in accordance with the general method of example 1 from cycloundecanone and 1-phenyl-1,3,8-triazaspiro[4,5]decan-4-one.

EXAMPLE 39

8-(cis-2,3,3a,4,5,9b-Hexahydro-1H-cyclopentafainaphthalen-2-yl)-1-phenyl-1,3,8-triaza-spiro[4,5]decan-4-one hydrochloride (1:1) (mixture of diastereoisomers)

The title compound, white solid, m.p. 217° C. (dec.) and MS: m/e=402.4 (M+H⁺) was prepared in accordance with the general method of example 1 from cis-1,3,3a,4,5,9b-hexahydro-1H-cyclopenta[a]naphthalen-2-one and 1-phenyl-1,3,8-triazaspiro[4,5]decan-4-one.

EXAMPLE 40

8-(2,3,4 5-Tetrahydro-cyclopentafalnarhthalen-2-yl)-1-phenyl-1,3,8-triaza-spiro[4,5]decan-4-one hydrochloride (1:1)

The title compound, white solid, m.p.>250° C. and MS: m/e=400.4 (M+H⁺) was prepared in accordance with the general method of example 1 from 1,3,4,5-tetrahydro-cyclopenta[a]naphthalen-2-one and 1-phenyl-1,3,8-triazaspiro[4,5]decan-4-one.

EXAMPLE 41

8-(cis-Octahydro-inden-2-yl)-1-phenyl-1,3,8-triaza-spiro[4,5]decan-4-one hydrochloride (1:1)

The title compound, white solid, m.p. 271° C. (dec.) and MS: m/e=354.4 (M+H⁺) was prepared in accordance with the general method of example 1 from cis-octahydro-inden-2-one and 1-phenyl-1,3,8-triazaspiro[4,5]decan-4-one.

EXAMPLE 42

8-(4a,10a-cis-1,2,3,4,4a,9,10,10a-Octahydro-phenanthren-3-yl)-1-phenyl-1,3,8-triaza-spiro[4,5]decan-4-one hydrochloride (1:1) (mixture of diastereoisomers)

The title compound, white solid, m.p. 257° C. and MS: m/e=416.2 (M+H⁺) was prepared in accordance with the general method of example 1 from (RS)-cis-1,4,4a,9,10,10a-hexahydro-2H-phenanthren-3-one and 1-phenyl-1,3,8-triazaspiro[4,5]decan-4-one.

EXAMPLE 43

8-(cis-Octahydro-inden-1-yl)-1-phenyl-1,3,8-triaza-spiro[4,5]decan-4-one hydrochloride (1:1) (mixture of diastereoisomers)

The title compound, white solid, m.p. 242° C. and MS: m/e=354.3 (M+H⁺) was prepared in accordance with the general method of example 1 from (RS)-cis-octahydro-inden-1-one and 1-phenyl-1,3,8-triazaspiro[4,5]decan-4-one.

EXAMPLE 44

8-(cis-Decahydro-azulen-1-yl)-1-phenyl-1,3,8-triaza-spiro[4,5]decan-4-one hydrochloride (1:1) (mixture of diastereoisomers)

The title compound, white solid, m.p. 259° C. and MS: m/e=368.3 (M+H⁺) was prepared in accordance with the general method of example 1 from (RS)-cis-octahydro-azulen-1-one and 1-phenyl-1,3,8-triazaspiro[4,5]decan-4-one.

EXAMPLE 45

8-Cyclodecyl-3-methyl-1-phenyl-1,3,8-triaza-spiro[4,5]decan-4-one hydrochloride (1:1)

The title compound, white solid, m.p. 248° C. (dec.) and MS: m/e=384.3 (M+H⁺) was prepared in accordance with the general method of example 24 from 8-cyclodecyl-1-phenyl-1,3,8-triaza-spiro[4 ,5]decan-4-one hydrochloride and methyl iodide.

EXAMPLE 46

8-Cyclodecyl-3-ethyl-1-phenyl-1,3,8-triaza-spiro[4,5]decan-4-one hydrochloride (1:1)

The title compound, white solid, m.p. 197° C. (dec.) and MS: m/e=398.4 M+H⁺) was prepared in accordance with the general method of example 24 from 8-cyclodecyl-1-phenyl-1,3,8-triaza-spiro[4,5]decan-4-one hydrochloride and ethyliodide.

EXAMPLE 47

8-Cyclodecyl-3-benzyl-1-nhenyl-1,3,8-triaza-spiro
[4,5]decan-4-one hydrochloride (1:1)

The title compound, white solid, m.p. 217° C. (dec.) and MS: m/e=460.4 (M+H$^+$) was prepared in accordance with the general method of example 24 from 8-cyclodecyl-1-phenyl-1,3,8-triaza-spiro[4,5]decan-4-one hydrochloride and benzyibromide. Example 48

8-Cyclodecyl-3-(3-phenyl-1-propyl)-1-phenyl-1,3,8-triaza-spiro[4,5]decan-4-one hydrochloride (1:1)

The title compound, white solid, m.p. 164° C. and MS: m/e=488.4 (M+H$^+$) was prepared in accordance with the general method of example 24 from 8-cyclodecyl-1-phenyl-1,3,8-triaza-spiro[4,5]decan-4-one hydrochloride and 3-phenyl-1-propylbromide.

EXAMPLE 49

8-Cyclodecyl-3-(3,3-diphenyl-1-propyl)-1-phenyl-1,3,8-triaza-spiro[4,5]decan-4-one hydrochloride (1:1)

The title compound, white solid, m.p. 219° C. and MS: m/e=564.5 (M+H$^+$) was prepared in accordance with the general method of example 24 from 8-cyclodecyl-1-phenyl-1,3,8-triaza-spiro[4,5]decan-4-one hydrochloride and 3,3-diphenyl-1-propylbromide.

EXAMPLE 50

8-(1-Isopropyl-4-methyl-bicyclo3,1.0-hex-3-yl)-1-phenyl-1,3,8-triaza-spiro[4,5]decan-4-one
hydrochloride (1:1) (mixture of diastereoisomers)

The title compound, white solid, m.p. 275° C. and MS: m/e=368.3 (M+H$^+$) was prepared in accordance with the general method of example 8 from a/b-thujone and 1-phenyl-1,3,8-triazaspiro[4,5]decan-4-one.

EXAMPLE 51

(RS)-8-[Spiro(5,5)undecan-2-yl]-1-phenyl-1,3,8-triaza-spiro[4,5]decan-4-one hydrochloride (1:1)

The title compound, white solid, m.p. 289° C. (dec.) and MS: m/e=381 (M$^+$) was prepared in accordance with the general method of example 8 from spiro (5,5)undecan-2-one and 1-phenyl-1,3,8-triazaspiro[4,5]decan-4-one.

EXAMPLE 52

8-(Decahydro-azulen-2-yl)-1-phenyl-1,3,8-triaza-spiro[4,5]decan-4-one hydrochloride (1:1) (mixture
of diastereoisomers)

The title compound, white solid, m.p. 272° C. and MS: m/e=368.3 (M+H$^+$) was prepared in accordance with the general method of example 1 from (RS)-octahydro-azulen-2-one and 1-phenyl-1,3,8-triazaspiro[4,5]decan-4-one.

EXAMPLE 53

Mixture of cis- and trans 1-Phenyl-8-(4-trifluoromethyl-cyclohexyl)-1,3,8-triaza-spiro[4,5]
decan-4-one hydrochloride (1:1)

The title compound, m.p.>250° C. and MS: m/e=382.2 (M+H$^+$) was prepared in accordance with the general method of example 1 from 4-trifluoromethylcyclohexanone and 1-phenyl-1,3,8-triazaspiro[4,5]decan-4-one.

EXAMPLE 54 cis-8-(4-Isopropyl-cyclohexyl)-1-phenyl-1,3,8-triaza-spiro[4,5]decan-4-one hydrochloride (1:1)

The title compound, m.p.>250° C. and NMR (DMSO-d$_6$): 0.88 (d, 6H), 2.0–1.1 (m, 12 H), 2.97 (t, 2H), 3.25 (m, 1H), 3.47 (m, 2H), 3.67 (m, 2H), 4.62 (s, 2H), 6.79 (t, 1H), 7.08 (d, 2H), 7.22 (t, 2H), 9.02 (s, 1H), 10.30 (bs, 1H) was isolated by preparative HPLC of the mixture obtained in example 31.

EXAMPLE 55 trans-8-(4-Isopropyl-cyclohexyl)-1-phenyl-1,3,8-triaza-spiro[4,5]decan-4-one hydrochloride (1:1)

The title compound, m.p.>250° C. and NMR (DMSO-d$_6$): 0.85 (d, 6H), 1.05 (m, 3H), 1.48 (m, 3H), 1.83 (m, 4H), 2.13 (m, 2H), 2.97 (t, 2H), 3.16 (m, 1H), 3.4 (m, 2H), 3.70 (m, 2H), 4.62 (s, 2H), 6.79 (t, 1H), 7.08 (d, 2H), 7.22 (t, 2H), 9.02 (s, 1H), 10.50 (bs, 1H) was isolated by preparative HPLC of the mixture obtained in example 31.

EXAMPLE 56

(R,S)-8-Cyclodecyl-1-phenyl-2-methyl-1,3,8-triaza-spiro[4,5]decan-4-one hydrochloride (1:1)

8-Benzyl-1-phenyl-1,3,8,-triaza-spiro[4,5]dec-2-en-4-on (1 g, 3.2 mMol) and some crystals of Cu(I)-chloride was dissolved in 50 ml dry THF and methylmagnesiumchloride (2.1 ml of a 3M solution in THF) was added dropwise. The reaction was stirred at RT until the TLC showed the absence of starting-material. To the reaction mixture was added 50 ml of a saturated ammonium-chloride solution and stirred for 30 minutes. Then the layers were separated and the aqueous layer was extracted three times with ethyl-acetate.The combined organic layers were dried over sodium sulfate, filtered and evaporated to give 1.05 g of (R,S)-8-benzyl-2-methyl-1-phenyl-1,3,8,-triaza-spiro[4,5] decan-4-on as slight yellow glass, m.p. 64.3–65.8° C., suitable clean for the next step. 1.05 g of this compound was dissolved in 30 ml methanol, 300 mg of Pd/C 10% was added and a balloon with hydrogen was attached. When TLC indicated the absence of starting material, the reaction mixture was filtered and evaporated to yield 617 mg of 2-methyl-1-phenyl-1,3,8,-triaza-spiro[4,5]decan-4-on as a slightly yellow foam. MS: 246 ((M+H)$^+$), suitable clean for the next reaction. 617 mg of this compound were dissolved in THF and 2.2 ml tetraisopropylortho-titanate and 2.8 mmol cyclodecanon was added. After 18 h at roomtemperature, the mixture was evaporated and the residue dissolved in ethanol and 2.5 mMol of sodiumcyano-borohydride was added. After 18 h at room-temperature, water and ethyl acetate was added, the layers separated and the organic layer washed with 2N aqueous sodium hydroxide solution and brine. The organic layer was dried over sodium sulfate, filtered and evaporated. Chromatography on silica-gel (ethyl-acetate) yielded the desired product which was crystallized as its hydrochloride salt from methanol/ether. 41 mg of (R,S)-8-Cyclodecyl-1-phenyl-2-methyl-1,3,8-triaza-spiro[4,5] decan-4-one hydrochloride (1:1) as an off-white powder, m.p.>250° C., MS: m/e=384 ((M+H)$^+$).

EXAMPLE 57

(R,S)-8-Cyclodecyl-1,2-diphenyl-1,3,8-triaza-spiro
[4,5]decan-4-one hydrochloride (1:1)

The title compound, m.p.>250° C., MS: m/e=446 ((M+H)$^+$), was prepared in accordance with the general method of

EXAMPLE 58

(R,S)-8-Cyclodecyl-1-(4-methyl-phenyl)-2-butyl-1, 3,8-triaza-spiro[4,5]decan-4-one hydrochloride (1:1)

The title compound, white crystals, MS: m/e=440 ((M+H)$^+$), was prepared in accordance with the general method of example 56 from 8-benzyl-1-(4-methyl-phenyl)-1,3,8,-triaza-spiro[4,5]dec-2-en-4-on, butyl-magnesium chloride and cyclodecanone.

EXAMPLE 59

(R,S)-8-Cyclodecyl-1-(2-methyl-phenyl)-2-butyl-1, 3,8-triaza-spiro[4,5]decan-4-one hydrochloride (1:1)

The title compound, yellow powder, MS: m/e=440 ((M+H)$^+$), was prepared in accordance with the general method of example 56 from 8-benzyl-1-(2-methyl-phenyl)-1,3,8,-triaza-spiro[4,5]dec-2-en-4-on, butyl-magnesium chloride and cyclodecanone.

EXAMPLE 60

(R,S)-8-Cyclodecyl-1-(3-methyl-phenyl)-2-phenyl-1, 3,8-triaza-spiro[4,5]decan-4-one hydrochloride (1:1)

The title compound, white crystals, MS: m/e=460 ((M+H)$^+$), was prepared in accordance with the general method of example 56 from 8-benzyl-1-(3-methyl-phenyl)-1,3,8,-triaza-spiro[4,5]dec-2-en-4-on, phenyl-magnesium chloride and cyclodecanone.

EXAMPLE 61

(R,S)-8-Cyclodecyl-1-(3-methyl-phenyl)-2-methyl-1,3,8-triaza-spiro[4,5]decan-4-one hydrochloride (1:1)

The title compound, white crystals, m.p. >250° C., MS: m/e=398 ((M+H)$^+$), was prepared in accordance with the general method of example 56 from 8-benzyl-1-(3-methyl-phenyl)-1,3,8,-triaza-spiro[4,5]dec-2-en-4-on, methyl-magnesium chloride and cyclodecanone.

EXAMPLE 62

(R,S)-8-Cyclodecyl-1-(3-methyl-phenyl)-2-butyl-1, 3,8-triaza-spiro[4,5]decan-4-one hydrochloride (1:1)

The title compound, off-white crystals, m.p. >250° C., MS: m/e=440 ((M+H)$^+$), was prepared in accordance with the general method of example 56 from 8-benzyl-1-(3-methyl-phenyl)-1,3,8,-triaza-spiro[4,5]dec-2-en-4-on, butyl-magnesium chloride and cyclodecanone.

EXAMPLE 63

8-Cyclodecyl-1-(2-methyl-phenyl)-1,3,8-triaza-spiro[4,5]decan-4-one hydrochloride (1:1)

The title compound, yellow crystals, MS: m/e=384 ((M+H)$^+$), was prepared in accordance with the general method of example 1 from 1-(2-methyl-phenyl)-1,3,8,-triaza-spiro[4,5]decan-4-on and cyclodecanone.

EXAMPLE 64

8-Cyclodecyl-1-(4-methyl-phenyl)-1,3,8-triaza-spiro[4,5]decan-4-one hydrochloride (1:1)

The title compound, yellow crystals, MS: m/e=384 ((M+H)$^+$), was prepared in accordance with the general method of example 1 from 1-(4-methyl-phenyl)-1,3,8,-triaza-spiro[4,5]decan-4-on and cyclodecanone.

EXAMPLE 65

8-(Dodecahydro-acenaphthylen-1-yl)-1-phenyl-1,3, 8-triaza-spiro[4,5]decan-4-one hydrochloride (1:1) (mixture of diastereoisomers)

The title compound, white solid, m.p. 265° C. and MS: m/e=394.3 (M+H$^+$) was prepared in accordance with the general method of example 8 from racdodecahydro-acenaphthylen-1-one and 1-phenyl-1,3,8-triazaspiro[4,5]decan-4-one.

EXAMPLE 66

8-(cis-Bicyclo[6.2.0]dec-9-yl)-1-phenyl-1,3,8-triaza-spiro[4,5]decan-4-one hydrochloride (1:1) (mixture of diastereoisomers)

The title compound, white solid, m.p. 242° C. and MS: m/e=368.3 (M+H$^+$) was prepared in accordance with the general method of example 8 from (RS)-cis-bicyclo[6.2.0]dec-9-one and 1-phenyl-1,3,8-triazaspiro[4,5]decan-4-one.

EXAMPLE 67 cis-8-(4-Cyclohexyl-cyclohexyl)-1-phenyl-1,3,8-triaza-spiro[4,5]decan-4-one hydrochloride (1:1)

The title compound, m.p. >250° C. and NMR (DMSO-d$_6$): 0.80 (m, 2H), 2.0–1.1 (m, 20 H), 2.97 (t, 2H), 3.25 (m,1H), 3.47 (m, 2H), 3.70 (m, 2H), 4.62 (s, 2H), 6.80 (t, 1H), 7.05 (d, 2H), 7.22 (t, 2H), 9.02 (s, 1H), 10.0 (bs, 1H) was isolated by preparative HPLC of the mixture obtained in example 30.

EXAMPLE 68 trans-8-(4-Propyl-cyclohexyl)-1-phenyl-1,3,8-triaza-spiro[4,5]decan-4-one hydrochloride (1:1)

The title compound, m.p. >250° C. and NMR (DMSO-d$_6$): 0.86 (t, 3H), 1.6–0.9 (m, 10 H), 1.85 (d, 4H), 2.15 (d, 2H), 3.0 (t, 2H), 3.20 (m, 1H), 3.43 (m, 2H), 3.70 (m, 2H), 4.62 (s, 2H), 6.78 (t, 1H), 7.05 (d, 2H), 7.18 (t, 2H), 9.02 (s, 1H), 10.55 (bs, 1H) was isolated by preparative HPLC of the mixture obtained in example 16.

EXAMPLE 69 cis-8-(4-Propyl-cyclohexyl)-1-phenyl-1,3,8-triaza-spiro[4,5]decan-4-one hydrochloride (1:1)

The title compound, m.p. >250° C. and NMR (DMSO-d$_6$): 0.89 (t, 3H), 2.0–1.1 (m, 15 H), 2.95 (t, 2H), 3.15 (m, 1H), 3.45 (m, 2H), 3.70 (m, 2H), 4.62 (s, 2H), 6.78 (t, 1H), 7.08 (d, 2H), 7.22 (t, 2H), 9.02 (s,1H), 10.40 (bs, 1H) was isolated by preparative HPLC of the mixture obtained in example 16.

EXAMPLE 70

(2RS,4aRS,8aSR)-8-(decahydro-naphthalen-2-yl)-1-phenyl-1,3,8-triaza-spiro[4,5]decan-4-one hydrochloride (1:1)

1-(2RS,4aRS,8aSR-Decahydro-naphthalen-2-yl)-4-phenylamino-piperidine-4-carboxylic acid amide (8 mmol) suspended in formamide (40 ml) was stirred for 2 h at 200°

C. The mixture was cooled, poured into cold water (400 ml) and extracted with methylene chloride. Organic phases were pooled, dried with sodium sulfate and concentrated to yield a mixture of (2RS,4aRS,8aSR)-8-(decahydro-naphthalen-2-yl)-1-phenyl-1,3,8-triaza-spiro[4,5]decan-4-one and (2RS, 4aRS,8aSR)-8-(decahydronaphthalen-2-yl)-1-phenyl-1,3,8-triaza-spiro[4,5]dec-2-en-4-one. This mixture was dissolved in methanol (60 ml) and sodiumborohydride (12 mmol) was added. The mixture was stirred for 1 h at 60° C., cooled and concentrated. Saturated ammonium chloride solution and methylene chloride were added to the residue. The water phase was extracted with methylene chloride. Organic phases were pooled, dried with sodium sulfate and concentrated. Chromatography on silica gel (methylene chloride/methanol, 98:2) yielded the desired product. This was crystallized as its HCl-salt from ethylacetate/ethanol. 0.65 g (22%) of (2RS,4aRS,8aSR)-8-(decahydronaphthalen-2-yl)-1-phenyl-1,3,8-triaza-spiro[4,5]decan-4-one hydrochloride (1:1), m.p. >250° C. and MS: m/e=368.2 (M+H$^+$).

EXAMPLE 71

8-Cyclodecyl-3-(3-methoxy-benzyl)-1-phenyl-1,3,8-triaza-spiro[4,5]decan-4-one hydrochloride (1:1)

The title compound, white solid, m. p. 175° C. and MS: m/e=490.4 (M+H$^+$) was prepared in accordance with the general method of example 24 from 8-cyclodecyl-1-phenyl-1,3,8-triaza-spiro[4,5]decan-4-one hydrochloride and 3-methoxybenzylchloride.

EXAMPLE 72

8-Cyclodecyl-3-(4,6-dimethoxy-[1,3,5]triazin-2-yl)-1-phenyl-1,3,8-triaza-spiro[4,5]decan-4-one hydrochloride (1:1)

The title compound, white solid, m. p. 216° C. and MS: m/e=509.5 (M+H$^+$) was prepared in accordance with the general method of example 24 from 8-cyclodecyl-1-phenyl-1,3,8-triaza-spiro[4,5]decan-4-one hydrochloride and 2-chloro-4,6-dimethoxy-[1,3,5]triazine.

EXAMPLE 73

8-Cyclodecyl-1-phenyl-3-(4-phenyl-butyl)-1,3,8-triaza-spiro[4,5]decan-4-one hydrochloride (1:1)

The title compound, white solid, m. p. 115° C. and MS: m/e=502.5 (M+H$^+$) was prepared in accordance with the general method of example 24 from 8-cyclodecyl-1-phenyl-1,3,8-triaza-spiro[4,5]decan-4-one hydrochloride and methanesulfonic acid 4-phenyl-but-1-yl ester.

EXAMPLE 74

(8-Cyclodecyl-4-oxo-1-phenyl-1,3,8-triaza-spiro[4,5]dec-3-yl)-acetonitrile hydrochloride (1:1)

The title compound, white solid, m. p. 240° C. and MS: m/e=409.3 (M+H$^+$) was prepared in accordance with the general method of example 24 from 8-cyclodecyl-1-phenyl-1,3,8-triaza-spiro[4,5]decan-4-one hydrochloride and bromoacetonitrile.

EXAMPLE 75

8-Cyclodecyl-1-phenyl-3-(2-piperidin-1-yl-ethyl)-1,3,8-triaza-spiro[4,5]decan-4-one hydrochloride (1:2)

The title compound, white solid, m. p. 245° C. and MS: m/e=481.5 (M+H$^+$) was prepared in accordance with the general method of example 24 from 8-cyclodecyl-1-phenyl-1,3,8-triaza-spiro[4,5]decan-4-one hydrochloride and 1-(2-chloroethyl)piperidine.

EXAMPLE 76

8-Cyclodecyl-3-naphthalen-1-ylmethyl-1-phenyl-1,3,8-triaza-spiro[4,5]decan-4-one hydrochloride (1:1)

The title compound, white solid, m. p. 210° C. and MS: m/e=510.4 (M+H$^+$) was prepared in accordance with the general method of example 24 from 8-cyclodecyl-1-phenyl-1,3,8-triaza-spiro[4,5]decan-4-one hydrochloride and 1-chloromethylnaphthaline.

EXAMPLE 77

8-Cyclodecyl-3-cyclopentyl-1-phenyl-1,3,8-triaza-spiro[4,5]decan-4-one hydrochloride (1:1)

The title compound, white solid, m. p. 221° C. and MS: m/e=438.3 (M+H$^+$) was prepared in accordance with the general method of example 24 from 8-cyclodecyl-1-phenyl-1,3,8-triaza-spiro[4,5]decan-4-one hydrochloride and bromocyclopentane.

EXAMPLE 78

8-Cyclodecyl-1-phenyl-3-(3-trifluoromethyl-benzyl)-1,3,8-triaza-spiro[4,5]decan-4-one hydrochloride (1:1)

The title compound, white solid, m. p. 197° C. and MS: m/e=528.3 (M+H$^+$) was prepared in accordance with the general method of example 24 from 8-cyclodecyl-1-phenyl-1,3,8-triaza-spiro[4,5]decan-4-one hydrochloride and 3-trifluoromethylbenzylchloride.

EXAMPLE 79

8-Cyclodecyl-1-phenyl-3-(3-piperidin-1-yl-propyl)-1,3,8-triaza-spiro[4,5]decan-4-one hydrochloride (1:2)

The title compound, white solid, m. p. 180° C. and MS: m/e=495.3 (M+H$^+$) was prepared in accordance with the general method of example 24 from 8-cyclodecyl-1-phenyl-1,3,8-triaza-spiro[4,5]decan-4-one hydrochloride and methanesulfonic acid 3-(1-piperidino)-prop-1-yl ester.

EXAMPLE 80

8-Cyclodecyl-3-cyclopropylmethyl-1-phenyl-1,3,8-triaza-spiro[4,5]decan-4-one hydrochloride (1:1)

The title compound, white solid, m. p. 214° C. and MS: m/e=424.3 (M+H$^+$) was prepared in accordance with the general method of example 24 from 8-cyclodecyl-1-phenyl-1,3,8-triaza-spiro[4,5]decan-4-one hydrochloride and bromomethylcyclopropane.

EXAMPLE 81

8-Cyclodecyl-1-phenyl-3-pyridin-3-ylmethyl-1,3,8-triaza-spiro[4,5]decan-4-one hydrochloride (1:2)

The title compound, white solid, m. p. 227° C. and MS: m/e=461.3 (M+H$^+$) was prepared in accordance with the general method of example 24 from 8-cyclodecyl-1-phenyl-1,3,8-triaza-spiro[4,5]decan-4-one hydrochloride and 3-chloromethyl-pyridine.

EXAMPLE 82

8-Cyclodecyl-3-(2-morpholin-4-yl-ethyl)-1-phenyl-1,3,8-triaza-spiro[4,5]decan-4-one hydrochloride (1:2)

The title compound, white solid, m. p. 190° C. and MS: m/e=483.6 (M+H$^+$) was prepared in accordance with the general method of example 24 from 8-cyclodecyl-1-phenyl-1,3,8-triaza-spiro[4,5]decan-4-one hydrochloride and N-(2-chloroethyl)-morpholine.

EXAMPLE 83

8-Cyclodecyl-3-(2-[1,3]dioxolan-2-yl-ethyl)-1-phenyl-1,3,8-triaza-spiro[4,5]decan-4-one hydrochloride (1:1)

The title compound, white solid, m. p. 205° C. and MS: m/e=470.6 (M+H$^+$) was prepared in accordance with the general method of example 24 from 8-cyclodecyl-1-phenyl-1,3,8-triaza-spiro[4,5]decan-4-one hydrochloride and 2-(2-bromoethyl)-1,3-dioxolane.

EXAMPLE 84

8-Cyclodecyl-3-[2-(5-methyl-2-phenyl-oxazol-4-yl)-ethyl]-1-phenyl-1,3,8-triaza-spiro[4,5]decan-4-one hydrochloride (1:1)

The title compound, white solid, m. p. 140° C. and MS: m/e=555.3 (M+H$^+$) was prepared in accordance with the general method of example 24 from 8-cyclodecyl-1-phenyl-1,3,8-triaza-spiro[4,5]decan-4-one hydrochloride and methanesulfonic acid 2-(5-methyl-2-phenyloxazol-4-yl)-ethyl ester.

EXAMPLE 85

8-Cyclodecyl-1-phenyl-3-(2-pvrrolidin-1-vI-ethyl)-1,3,8-triaza-spiro[4,5]decan-4-one hydrochloride (1:2)

The title compound, white solid, m. p. 179° C. and MS: m/e=467.3 (M+H$^+$) was prepared in accordance with the general method of example 24 from 8-cyclodecyl-1-phenyl-1,3,8-triaza-spiro[4,5]decan-4-one hydrochloride and 1-(2-chloroethyl)-pyrrolidine.

EXAMPLE 86

8-Cyclodecyl-3-(2-oxo-oxazolidin-5-ylmethyl)-1-phenyl-1,3,8-triaza-spiro[4,5]decan-4-one hydrochloride (1:1)

The title compound, white solid, m. p. 174° C. and MS: m/e=469.3 (M+H$^+$) was prepared in accordance with the general method of example 24 from 8-cyclodecyl-1-phenyl-1,3,8-triaza-spiro[4,5]decan-4-one hydrochloride and 5-chloromethyl-2-oxazolidinone.

EXAMPLE 87

(R,S)-8-Cyclodecyl-1-(4-methyl-phenyl)-2-methyl-1,3,8-triaza-spiro[4,5]decan-4-one hydrochloride (1:1)

The title compound, white crystals, MS: m/e=398 ((M+H)$^+$), was prepared in accordance with the general method of example 56 from 8-benzyl-1-(4-methyl-phenyl)-1,3,8,-triaza-spiro[4,5]dec-2-en-4-on, methyl-magnesium chloride and cyclodecanone

EXAMPLE 88

(8-Cyclodecyl-4-oxo-1-phenyl-1,3,8-triaza-spiro[4,5]dec-3-yl)-acetic acid methyl ester hydrochloride (1:1)

The title compound, white solid, m. p. 178° C. and MS: m/e=442.5 (M+H$^+$) was prepared in accordance with the general method of example 24 from 8-cyclodecyl-1-phenyl-1,3,8-triaza-spiro[4,5]decan-4-one hydrochloride and bromomethyl acetate.

EXAMPLE 89

2-(8-Cyclodecyl-4-oxo-1-phenyl-1,3,8-triaza-spiro[4,5]dec-3-yl)-acetamide hydrochloride (1:1)

(8-Cyclodecyl-4-oxo-1-phenyl-1,3,8-triaza-spiro[4,5]dec-3-yl)-acetic acid methyl ester (0.7 mmol) was dissolved in a 9M solution of ammonia in methanol (5 ml). The reaction mixture was shaken overnight in a closed tube at 50° C. After evaporation of the solvent the desired product remained as a white foam. Formation of the HCl-salt yielded 0.255 g of the title compound as a white solid, m. p. >250° C. and MS: m/e=427.5 (M+H$^+$).

EXAMPLE 90

2-(8-Cyclodecyl-4-oxo-1-phenyl-1,3,8-triaza-spiro[4,5]dec-3-yl)-N,N-dimethyl-acetamide hydrochloride (1:1)

The title compound, white solid, m. p. 145° C. and MS: m/e=455.6 (M+H$^+$) was prepared in accordance with the general method of example 24 from 8-cyclodecyl-1-phenyl-1,3,8-triaza-spiro[4,5]decan-4-one hydrochloride and N,N-dimethyl-2-chioroacetamide.

EXAMPLE 91

8-Cyclodecyl-3-(2-hydroxy-ethyl)-1-phenyl-1,3,8-triaza-spiro[4,5]decan-4-one hydrochloride (1:1)

(8-Cyclodecyl-4-oxo-1-phenyl-1,3,8-triaza-spiro[4,5]dec-3-yl)-acetic acid methyl ester (0.8 mmol) was dissolved in ethyleneglycol dimethylether (2 ml). Lithiumchloride (0.8 mmol) and sodium borohydride (0.8 mol) were added. After stirring for 4 h the reaction mixture was distributed between dichloromethane/water/methanol. The organic layer was separated, dried over magnesium sulfate and evaporated. The residue was purified by column chromatography (SiO2, ethyl acetate). Formation of the HCl-salt yielded the title compound as a white solid, 0.124 g, m. p. 190° C. and MS: m/e=414.5 (M+H$^+$).

EXAMPLE 92

N-Benzyl-2-(8-cyclodecyl-4-oxo-1-phenyl-1,3,8-triaza-spiro[4,5]dec-3-yl)-acetamide hydrochloride (1:1)

(8-Cyclodecyl-4-oxo-1-phenyl-1,3,8-triaza-spiro[4,5]dec-3-yl)-acetic acid methyl ester (0.6 mmol) was dissolved in methanol (5 ml). After adding benzylamine (1.2 mmol) the reaction mixture was kept 4 days at room temperature. The solvent was evaporated and the residue was purified by column chromatography (SiO2, ethyl acetate). Formation of the HCl-salt yielded 0.255 g of the title compound as a white solid, 66 mg, m. p. 196° C. and MS: m/e=517.4 (M+H$^+$).

EXAMPLE 93

5-(8-Cyclodecyl-4-oxo-1-phenyl-1,3,8-triaza-spiro[4,5]dec-3-yl)-pentanoic acid ethyl ester hydrochloride (1:1)

The title compound, white solid, m. p. 170° C. and MS: m/e=498.5 (M+H$^+$) was prepared in accordance with the general method of example 24 from 8-cyclodecyl-1-phenyl-1,3,8-triaza-spiro[4,5]decan-4-one hydrochloride and ethyl 5-bromovaleriate.

EXAMPLE 94

1-Phenyl-8-(trans-4-trifluoromethyl-cyclohexyl)-1,3, 8-triaza-spiro[4,5]decan-4-one hydrochloride (1:1)

The title compound, m.p. >250° C. and NMR (DMSO-$d_6$): 1.39 (q, 2H), 1.62 (q, 2H), 1.88 (d, 2H), 2.01 (d, 2H), 2.24 (d, 2H), 2.33 (bs, 1H), 2.99 (t, 2H), 3.36 (m, 3H), 3.70 (m, 2H), 4.62 (s, 2H), 6.78 (t, 1H), 7.09 (d, 2H), 7.21 (t, 2H), 9.02 (s, 1H), was isolated by preparative LC of the mixture obtained in example 53.

EXAMPLE 95

Mixture of cis- and trans 1-Phenyl-8-(4-ethyl-cyclohexyl)-1,3,8-triaza-spiro[4,5]decan-4-one hydrochloride (1:1)

The title compound, m.p. >250° C. and NMR (DMSO-$d_6$): 0.86 (t, 3H), 0.9–2.0 (m, 12H), 2.20 (d, 1H), 3.1 (m, 3H), 3.4 (m, 2H), 3.70 (m, 2H), 4.62 (s, 2H), 6.77 (t, 1H), 7.11 (d, 2H), 7.19 (t, 2H), 9.02 (s, 1H), 10.7 (bs, 1H) was prepared in accordance with the general method of example 1 from 4-ethyl-cyclohexanone and 1-phenyl-1,3,8-triaza-spiro[4,5]decan-4-one.

EXAMPLE 96

(2RS,4aSR,8aRS)-8-(Decahydro-naphthalen-2-yl)-1-phenyl-1,3,8-triaza-spiro[4,5]decan-4-one hydrochloride (1:1)

The title compound, m.p. >250° C. and NMR (DMSO-$d_6$): 1.1–2.0 (m, 18H), 3.02 (t, 2H), 3.2 (bs, 1H), 3.45 (m, 2H), 3.70 (m, 2H), 4.62 (s, 2H), 6.78 (t, 1H), 7.10 (d, 2H), 7.19 (t, 2H), 9.03 (s, 1H), 10.6 (bs, 1H) was prepared in accordance with the general methods used to prepare example 70 but from 1-(2RS,4aSR,8aRS-decahydro-naphtalen-2-yl)-piperidin-4-one.

EXAMPLE 97

1:1-mixture of cis and trans 4-Isopropyl-1-(4-oxo-1-phenyl-1,3,8-triazaspiro[4,5]dec-8-yl)-cyclohexanecarbonitrile 4-Isopropyl-cyclohenanone (1.4 g) and 1-phenyl-1,3,8-triazaspiro[4,5]decane-4-one were dissolved in 25 ml of acetic acid. To this was added, via syringe under argon, 1.25 ml of trimethylsilyl-cyanide. The mixture was stirred for 18 h at room temperature after which another 1.25 ml of trimethylsilyl-cyanide was added. After 50 h at room temperature, the reaction mixture was poured on ice, adjusted to pH 9 using 30% aqueous ammonium hydroxide and extracted three times with ethyl acetate. The combined organic layers were dried over sodium sulfate, filtered and evaporated to yield the title compound, 1.35 g, as a white powder, m.p. 213–215° C., MS: m/e=381 (M+).

EXAMPLE 98

1:1-mixture of cis and trans 8-(4-Isproryl-1-methyl-cyclohexyl)-1-phenyl-1,3,8-triazaspiro[4,5]decane-4-one hydrocloride (1:1)

The 1:1-mixture of cis and trans 4-isopropyl-1-(4-oxo-1-phenyl-1,3,8-triazaspiro[4,5]dec-8-yl)-cyclohexanecarbonitrile (0.65 mmol) was dissolved in 15 ml dry tetrahydrofurane under argon. To this was added, at room temperature, 270 mL of a 3N solution of methylmagnesium chloride in tetrahydrofurane at a rate that the internal temperature did not raise above 25° C. After 15 h stirring at room temperature, the reaction was quenched by addition of saturated aqueous ammonium chloride, then adjusted to pH 11 using aqueous sodium hydroxide and extracted with ethyl acetate. The combined organic layers were dried over sodium sulfate, filtered, evaporated and chromatographed on silica gel using ethyl acetate:cyclohexane 2:1 as the eluent to give the title compound, 168 mg as an off-white powder. The hydrochloride had m.p. >250° C. (decomp.), MS: m/e=370 (M+).

EXAMPLE 99

1:1-mixture of cis and trans 8-(1,4-Diisopropyl-cyclohexyl)-1-phenyl-1,3,8-triazaspiro[4,5]decane-4-one hydrocloride (1:1)

The 1:1-mixture of cis and trans 4-isopropyl-1-(4-oxo-1-phenyl-1,3,8-triazaspiro[4,5]dec-8-yl)-cyclohexanecarbonitrile (1.5 mmol) was dissolved in 35 ml dry tetrahydrofurane under argon. This was added, at room temperature, to a freshly prepared solution of isopropylmagnesiumbromide (15 mmol) in tetrahydrofurane at a rate that the internal temperature did not raise above 25° C. After 15 h stirring at room temperature and 3 h at 70° C., the reaction was quenched by addition of saturated aqueous ammonium chloride, then adjusted to pH 11 using aqueous sodium hydroxide and extracted with ether. The combined organic layers were dried over sodium sulfate, filtered, evaporated to give the title compound, 265 mg as an off-white powder. The hydrochloride had m.p. >245° C. (decomp.), MS: m/e=398 (M+).

EXAMPLE 100

(RS)-2-Butyl-1-(4-chlorophenyl)-8-cyclodecyl-1,3, 8-triazaspiro[4,5]decan-4-one hydrochloride 1:1

The title compound, slightly yellow powder, m.p. 263.3–264.6, MS: m/e=461 (M+), was prepared in accordance to general example 56 from 8-benzyl-1-(4-chlorophenyl)-1,3,8-triazaspiro[4,5]dec-2-en-4-one, butyl-magnesiumchloride and cyclodecanone.

EXAMPLE 101

(RS)-2-Butyl-1-phenyl-8-cyclodecyl-1,3,8-triazaspiro[4,5]decan-4-one hydrochloride 1:1

The title compound, white powder, m.p. 275.9–276.8, MS: m/e=426 (M+), was prepared in accordance to general example 56 from 8-benzyl-1-phenyl-1,3,8-triazaspiro[4,5]dec-2-en-4-one, butyl-magnesiumchloride and cyclodecanone.

EXAMPLE 102

Mixture of 8-(cis-4-methylcyclohexyl)-1-(4-methylphenyl)-1,3,8-triazaspiro[4,5]decan-4-one hydrochoride 1:1 and 8-(trans-4-methylcyclohexyl)-1-(4-methylphenyl)-1,3,8-triazaspiro[4,5]decan-4-one hydrochoride 1:1

The title compound, white powder, m.p. >283° C., MS: m/e=342 (M+1+), was prepared in accordance to general example 8 from 1-(4-methylphenyl)-1,3,8-triazaspiro[4,5] decan-4-one and 4-methyl-cyclohexanone.

EXAMPLE 103

8-cyclodecyl-1-(2-methoxyphenyl)-1,3,8-triazaspiro [4,5]decan-4-one hydrochloride 1:1

The title compound, white powder, m.p. >2280° C. (decomp.), MS: m/e=400 (M+1$^+$), was prepared in accordance to general example 8 from 1-(2-methoxyphenyl)-1,3, 8-triazaspiro[4,5]decan-4-one and cyclodecanone.

EXAMPLE 104

8-(Bicyclo-nonan-9-yl)-1-phenyl-1,3,8-triaza-spiro [4,5]decan-4-one hydrochloride (1:1)

The title compound, white solid, m.p. 309° C. and MS: m/e=354.3 (M+H+) was prepared in accordance with the general method of example 8 from bicyclo-nonan-9-one and 1-phenyl-1,3,8-triazaspiro[4,5]decan-4-one.

Synthesis of Intermediates

EXAMPLE aa 1-(2RS,4aRS,8aSR-Decahydro-naphthalen-2-yl)-4-phenylamino-piperidine-4-carboxylic acid amide 1-(2RS,4aRS,8aSR-Decahydro-naphthalen-2-yl)-4-phenylamino-piperidine-4-carbonitrile (7 mmol) was added dropwise at room temperature to a mixture of acetic anhydride and formic acid (15 ml each). The mixture was stirred for 21 h at room temperature. Sodium hydroxide solution was added (pH=7) and the mixture extracted with ethylacetate. Organic phases were pooled, dried with sodium sulfate and concentrated. Chromatography on silica gel (ethylacetate) yielded the formylated amine which was dissolved in t-butanol (60 ml). Ammonia (28%, 10 ml), water (10 ml) and hydrogen peroxide solution (33% in water, 8 ml) were added. The mixture was stirred for 3.5 h at room temperature, quenched with cold water (75 ml) and extracted with methylene chloride. Organic phases were pooled, dried with sodium sulfate and concentrated. Chromatography on silica gel (methylene chloride/methanol, 98:2) yielded the desired product as a solid. 1.5 g (55%) of 1-(2RS,4aRS,8aSR-decahydro-naphthalen-2-yl)-4-phenylamino-piperidine-4-carboxylic acid amide, m.p.>150° C. dec. and MS: m/e=356.3 (M+H$^+$).

EXAMPLE ab 1-(2RS,4aRS,8aSR-Decahydro-naphthalen-2-yl)-4-phenylamino-piperidine-4-carbonitrile 1-(2RS,4aRS,8aSR-decahydro-naphthalen-2-yl)-piperidin-4-one (8 mmol) was dissolved in acetic acid (8 ml). Aniline (9 mmol) and trimethylsilylcyanide (8 mmol) were added and the mixture was stirred for 90 min at room temperature. The reaction mixture was poured into cold ammonia solution (water/28% ammonia, 70 ml/30 ml). The solution was adjusted to pH 10 and extracted with dichloromethane. Organic phases were pooled, dried with sodium sulfate and concentrated. Crystallization from diethylether yielded the desired product as a solid. 2.8 g (97%) of 1-(2RS,4aRS,8aSR-Decahydro-naphthalen-2-yl)-4-phenylamino-piperidine-4-carbonitrile, m.p. 153–156° C. and MS: m/e=338.3 (M+H$^+$).

EXAMPLE ac 1-(2RS,4aRS,8aSR-decahydro-naphthalen-2-yl)-piperidin-4-one (2RS,4aRS,8aSR)-Decahydro-2-naphthylamine (12 mmol) was dissolved in ethanol (30 ml). Potassium carbonate (7.4 mmol) and 1-ethyl-1-methyl-4-oxo-piperidinium iodide (19 mmol) dissolved in water (10 ml) were added and the mixture was refluxed for 1 h. Water was added, ethanol was removed in vacuo and the residue was extracted with ethylacetate. Organic phases were pooled, dried with sodium sulfate and concentrated. Chromatography on silica gel (ethylacetate) yielded the desired product as an oil. 2.0 g (71%) of 1-(2RS,4aRS,8aSR-decahydro-naphthalen-2-yl)-piperidin-4-one, MS: m/e=235 (M$^+$).

EXAMPLE ad

8-Benzyl-1-p-tolyl-1,3,8-triazaspiro[4,5]dec-2-en-4-one

1-Benzyl-4-piperidone (50 mMol, 9.46 g) and 4-methyl-aniline (50 mMol, 5.36 g) were dissolved in acetic acid (100 ml) and cooled to 0° C. Trimethylsilyl cyanide (100 mMol, 12.5 ml) was added at such a rate, that the temperature did not rise above 5° C. After 20 h at room temperature, the reaction mixture was poured on ice, adjusted to pH 10 using 30% aqueous ammonium hydroxide and extracted three times with dichloromethane. The combined organic layers were dried over sodium sulfate, filtered and evaporated to yield 4-(p-tolyl-amino)-1-phenylmethyl)-4-piperidine-carbonitrile (13.4g) as a slightly yellow powder which was recrystallized from cyclohexane. m.p. 116.5–117° C.

4-(p-tolyl-amino)-1-phenylmethyl)-4-piperidine-carbonitrile (4.58 g) was dissolved in 25 ml conc. sulfuric acid and stirred for 70 h at room temperature. Then the reaction mixture was poured on ice and adjusted to pH 10 by addition of 30% aqueous ammonium hydroxide and extracted three times with dichloromethane. The combined organic layers were dried over sodium sulfate, filtered and evaporated to yield 4-(p-tolyl-amino)-1-phenylmethyl)-4-piperidine-carboxamide as an off-white powder (5.11 g), m.p. 167.5–169° C.

4-(p-tolyl-amino)-1-(phenylmethyl)-4-piperidine-carboxamide (1.62 g) was dissolved in 10 ml triethyl orthoformate and stirred at 150° C. for 15 hours. After cooling to room temperature, the reaction mixture was filtered and the light brown powder washed with ether to yield 8-benzyl-1-p-tolyl-1,3,8-triazaspiro[4,5]dec-2-en-4-one (0.99 g). M.p. 208–213° C.

EXAMPLE ae

8-Benzyl-1-(4-chloro-phenyl)-1,3,8-triazaspiro[4,5] dec-2-en-4-one

1-Benzyl-4-piperidone (95 mMol, 16.9 ml) and 4-chloro-aniline (95 mMol, 12.1 g) were dissolved in acetic acid (100 ml) and cooled to 0° C. Trimethylsilyl cyanide (180 mMol, 22 ml) was added at such a rate, that the temperature did not rise above 5° C. After 4 d at room temperature, the reaction mixture was poured on ice, adjusted to pH 10 using 30% aqueous ammonium hydroxide and extracted three times with dichloromethane. The combined organic layers were dried over sodium sulfate, filtered and evaporated to yield 4-(4-chloro-phenyl-amino)-1-phenylmethyl)-4-piperidine-carbonitrile (30.3 g) as a slightly yellow powder, m.p. 142–150° C.

4-(4-chloro-phenyl-amino)-1-phenylmethyl)-4-piperidine-carbonitrile (29.3 g) was dissolved in 150 ml conc. sulfuric acid and stirred for 1 h at room temperature and 1 h at 70° C. Then the reaction mixture was cooled to room temperature and poured on ice, adjusted to pH 10 by addition of 30% aqueous ammonium hydroxide and extracted three times with dichloromethane. The combined organic layers were dried over sodium sulfate, filtered and evaporated to yield 4-(4-chloro-phenyl-amino)-1-phenylmethyl)-4-piperidine-carboxamide as an brownish oil which crystallized upon addition of 50 ml diethyl ether and 50 ml pentane. Off-white powder (11.84 g), m.p. 167–170° C.

4-(4-chloro-phenyl-amino)-1-(phenylmethyl)-4-piperidine-carboxamide (6.47 g) was dissolved in 31 ml triethyl orthoformate and stirred at 150° C. for 10 d. After cooling to 0° C., the reaction mixture was filtered and the light brown powder washed with ether to yield 8-benzyl-1-4-chloro-phenyl-1,3,8-triazaspiro[4,5]dec-2-en-4-one (3.90 g). M.p. 217–219° C.

EXAMPLE af

8-Benzyl-1-(-3-methyl-phenyl)-1,3,8-triazaspiro[4,5]dec-2-en-4-one

1-Benzyl-4-piperidone (100 mMol, 17.9 ml) and 3-methyl-aniline (100 mMol, 10.6 ml) were dissolved in acetic acid (100 ml) and cooled to 0° C. Trimethylsilyl cyanide (200 mMol, 25.5 ml) was added at such a rate, that the temperature did not rise above 5° C. After 3 d at room temperature, the reaction mixture was poured on ice, adjusted to pH 10 using 30% aqueous ammonium hydroxide and extracted three times with ethyl acetate. The combined organic layers were dried over sodium sulfate, filtered and evaporated to 50 ml, then treated with 50 ml diethyl ether and 50 ml pentane to yield 4-(3-methyl-phenyl-amino)-1-phenylmethyl)-4-piperidine-carbonitrile as a slightly yellow powder which was washed with ether and dried. 15.48 g, m.p. 95.7–97.1° C.

4-(3-methyl-phenyl-amino)-1-phenylmethyl)-4-piperidine-carbonitrile (15.48 g) was dissolved in 77 ml conc. sulfuric acid and stirred for 18 h at room temperature. After cooling to room temperature, the reaction mixture was poured on ice and adjusted to pH 10 by addition of 30% aqueous ammonium hydroxide and extracted three times with dichloromethane. The combined organic layers were dried over sodium sulfate, filtered and evaporated to yield off-white crystals of 4-(3-methyl-phenyl-amino)-1-phenylmethyl)-4-piperidine-carboxamide (14.46), m.p. 106.1–108.6° C.

4-(3-methyl-phenyl-amino)-1-(phenylmethyl)-4-piperidine-carboxamide (12.94 g) was dissolved in 80 ml triethyl orthoformate and stirred at 150° C. for 66 hours. After cooling to 0° C., the reaction mixture was filtered and the light brown powder washed with ether to yield 8-benzyl-1-(3-methyl-phenyl)-1,3,8-triazaspiro[4,5]dec-2-en-4-one (2.1g). M.p. 301.5–302.6° C.

EXAMPLE ag 8-benzyl-1-(-2-methyl-phenyl)-1,3,8-triazaspiro[4,5]dec-2-en-4-one

1-Benzyl-4-piperidone (100 mMol, 17.9 ml) and 2-methyl-aniline (100 mMol, 10.6 ml) were dissolved in acetic acid (100 ml) and cooled to 0° C. Trimethylsilyl cyanide (200 mMol, 25.5 ml) was added at such a rate, that the temperature did not rise above 5° C. After 3 d at room temperature, the reaction mixture was poured on ice, adjusted to pH 10 using 30% aqueous ammonium hydroxide and extracted three times with ethyl acetate. The combined organic layers were dried over sodium sulfate, filtered and evaporated to 50 ml and treated with 50 ml diethyl ether and 50 ml pentane to yield 4-(3-methyl-phenyl-amino)-1-phenylmethyl)-4-piperidine-carbonitrile as a slightly yellow powder which was washed with ether and dried. 18.89 g, m.p. 103.6–105.7° C.

4-(2-methyl-phenyl-amino)-1-phenylmethyl)-4-piperidine-carbonitrile (17.89 g) was dissolved in 88 ml conc. sulfuric acid and stirred for 3 d at room temperature. The reaction mixture was poured on ice and adjusted to pH 10 by addition of 30% aqueous ammonium hydroxide and extracted three times with dichloromethane. The combined organic layers were dried over sodium sulfate and evaporated to yield 4-(2-methyl-phenyl-amino)-1-phenylmethyl)-4-piperidine-carboxamide (10.35 g) as a brown oil. MS: m/z=324 (M+H)$^+$ 4-(2-methyl-phenyl-amino)-1-(phenylmethyl)-4-piperidine-carboxamide (10.35 g) was dissolved in 60 ml triethyl orthoformate and stirred at 150° C. for 10 d. After cooling to 0° C, the reaction mixture was evaporated and the resulting brown oil was chromatographed on silica gel using dichloromethane:methanol 19:1 as eluent. 8-benzyl-1-(2-methyl-phenyl)-1,3,8-triazaspiro[4,5]dec-2-en-4-one (4.71 g) was obtained as a brown foam. MS: m/z=334 (M+H)$^+$

EXAMPLE A

Tablets of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

We claim:

1. A compound having the formula

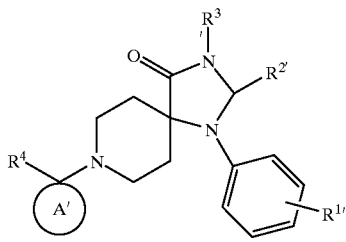

wherein $R^{1'}$ is hydrogen, $R^{2'}$ is hydrogen, $R^{3'}$ is hydrogen;

$R^4$ is a substituent at position 1 on A' and is selected from hydrogen, lower alkyl, or nitrilo; and A' is a ring system, consisting of (a): cyclohexyl, methyl-substituted cyclohexyl, isoyropyl-substituted cyclohexyl, cylononyl, or cyclodecyl; and pharmaceutically acceptable acid addition salts thereof.

2. A compound having the formula

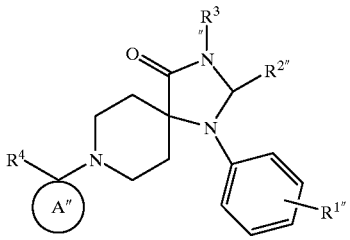

wherein $R^{1''}$ is hydrogen or methyl, $R^{2''}$ is hydrogen or phenyl, $R^{3'}$ is hydrogen or acetonitrile;

$R^4$ is a substituent at position 1 on A" and is selected from hydrogen, lower alkyl, or nitrilo; and A" is a ring system, consisting of (a) cyclodecyl; and pharmaceutically acceptable acid addition salts thereof.

3. The compound according to claim 1, 8-Cyclohexyl-1-phenyl-1,3,8-triaza-spiro[4,5]decan-4-one.

4. The compound according to claim 1, which is a mixture of (1RS,3RS)- and (1RS,3SR)-8-(3-methyl-cyclohexyl)-1-phenyl-1,3,8-triaza-spiro[4,5]decan-4-one.

5. The compound according to claim 1, which is a mixture of cis- and trans-8-(4-methyl-cyclohexyl)-1-phenyl-1,3,8-triaza-spiro[4,5]decan-4-one.

6. The compound according to claim 1, 1-Phenyl-8-(3,3,5,5-tetramethyl-cyclohexyl)-1,3,8-triaza-spiro[4,5]decan-4-one.

7. The compound according to claim 1, which is a mixture of (1RS,2RS)- and (1RS,2SR)-8-(2-methyl-cyclohexyl)-1-phenyl-1,3,8-triaza-spiro[4,5]decan-4-one.

8. The compound according to claim 1, which is a mixture of (1R,3R)- and (1S,3R)-8-(3-methyl-cyclohexyl)-1-phenyl-1,3,8-triaza-spiro[4,5]decan-4-one.

9. The compound according to claim 1, which is a mixture of (1RS,5RS)- and (1RS,5SR)-1-phenyl-8-(3,3,5-trimethyl-cyclohexyl)-1,3,8-triaza-spiro[4,5]decan-4-one.

10. The compound according to claim 1, cis-8-(4-Methyl-cyclohexyl)-1-phenyl-1,3,8-triaza-spiro[4,5]decan-4-one.

11. The compound according to claim 1, trans-8-(4-Methyl-cyclohexyl)-1-phenyl-1,3,8-triaza-spiro[4,5]decan-4-one.

12. The compound according to claim 1, cis-8-[4-(1,1-Dimethyl-propyl)-cyclohexyl]-1-phenyl-1,3,8-triaza-spiro[4,5]decan-4-one.

13. The compound according to claim 1, trans-8-[4-(1,1-Dimethyl-propyl)-cyclohexyl]-1-phenyl-1,3,8-triaza-spiro[4,5]decan-4-one.

14. The compound according to claim 1, which is a mixture of cis- and trans 8-(4-Isopropyl-cyclohexyl)-1-phenyl-1,3,8-triaza-spiro[4,5]decan-4-one.

15. The compound according to claim 1, 8-Cyclodecyl-1-phenyl-1,3,8-triaza-spiro[4,5]decan-4-one.

16. The compound according to claim 1, 8-Cyclononyl-1-phenyl-1,3,8-triaza-spiro[4,5]decan-4-one hydrochloride (1:1).

17. The compound according to claim 1, cis-8-(4-Isopropyl-cyclohexyl)-1-phenyl-1,3,8-triaza-spiro[4,5]decan-4-one.

18. The compound according to claim 1, trans-8-(4-Isopropyl-cyclohexyl)-1-phenyl-1,3,8-triaza-spiro[4,5]decan-4-one.

19. The compound according to claim 1, cis-8-(4-Propyl-cyclohexyl)-1-phenyl-1,3,8-triaza-spiro[4,5]decan-4-one.

20. The compound according to claim 2, (8-Cyclodecyl-4-oxo-1-phenyl-1,3,8-triaza-spiro[4,5]dec-3-yl)-acetonitrile.

21. The compound according to claim 1, which is present as a mixture of cis and trans 8-(4-Isopropyl-1-methyl-cyclohexyl)-1-phenyl-1,3,8-triazaspiro[4,5]decane-4-one.

22. The compound according to claim 1, which is present as a mixture of cis and trans 8-(1,4-Diisopropyl-cyclohexyl)-1-phenyl-1,3,8-triazaspiro[4,5]decane-4-one.

23. The compound according to claim 2, wherein $R^2$ is phenyl.

24. The compound according to claim 23, (R,S)-8-Cyclodecyl-1,2-diphenyl-1,3,8-triaza-spiro[4,5]decan-4-one.

25. The compound according to claim 2, wherein $R^1$ is lower alkyl.

26. The compound according to claim 25, wherein $R^2$ is hydrogen.

27. The compound according to claim 26, 8-Cyclodecyl-1-(2-methyl-phenyl)-1,3,8-triaza-spiro[4,5]decan-4-one.

28. The compound according to claim 27, 8-Cyclodecyl-1-(4-methyl-phenyl)-1,3,8-triaza-spiro[4,5]decan-4-one.

29. The compound according to claim 25, wherein $R^2$ is phenyl.

30. The compound according to claim 29, (R,S)-8-Cyclodecyl-1-(3-methyl-phenyl)-2-phenyl-1,3,8-triaza-spiro[4,5]decan-4-one.

* * * * *

UNITED STATES PATENT AND TRADEMARK OFFICE
CERTIFICATE OF CORRECTION

PATENT NO.   : 6,043,366
DATED        : March 28, 2000
INVENTOR(S)  : Adam et al.

It is certified that error appears in the above-identified patent and that said Letters Patent is hereby corrected as shown below:

On the title page item [75], correct "Caido Galley" to --Guido Galley--.

In the claims, column 36, claim 28, correct "claim 27" to --claim 26--.

Signed and Sealed this

Third Day of April, 2001

Attest:

NICHOLAS P. GODICI

*Attesting Officer*    *Acting Director of the United States Patent and Trademark Office*